United States Patent
Brophy et al.

(10) Patent No.: US 8,349,325 B2
(45) Date of Patent: Jan. 8, 2013

(54) SOLUBLE FMS-LIKE TYROSINE KINASE-1 (SFLT-1) ANTIBODY AND RELATED COMPOSITION, KIT, METHODS OF USING, AND MATERIALS AND METHOD FOR MAKING

(75) Inventors: Susan E. Brophy, Lindenhurst, IL (US); Saul A. Datwyler, Evanston, IL (US); David J. Hawksworth, Lake Villa, IL (US); Don C. Laird, Mundelein, IL (US); Sharmila Manoj, Arlington Heights, IL (US); Dominick L. Pucci, Libertyville, IL (US); Bryan C. Tieman, Elmhurst, IL (US); Joan Tyner, Beach Park, IL (US); Lowell J. Tyner, legal representative, Chicago, IL (US); Zhiguang Yu, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 226 days.

(21) Appl. No.: 12/643,847

(22) Filed: Dec. 21, 2009

(65) Prior Publication Data

US 2010/0266575 A1 Oct. 21, 2010

Related U.S. Application Data

(60) Provisional application No. 61/140,561, filed on Dec. 23, 2008.

(51) Int. Cl.
*A61K 39/395* (2006.01)
*C07K 16/18* (2006.01)
*C07K 16/28* (2006.01)

(52) U.S. Cl. ............... 424/133.1; 424/130.1; 424/141.1; 424/143.1; 530/387.1; 530/388.1; 530/388.2

(58) Field of Classification Search ........................ None
See application file for complete search history.

(56) References Cited

U.S. PATENT DOCUMENTS

| | | | |
|---|---|---|---|
| 5,294,404 A | 3/1994 | Grandone et al. |
| 6,855,508 B2 | 2/2005 | Fei et al. |
| 7,052,693 B2 | 5/2006 | Shitara et al. |
| 7,335,362 B2 | 2/2008 | Karumanchi et al. |
| 2004/0126828 A1 | 7/2004 | Karumanchi et al. |
| 2007/0218498 A1 | 9/2007 | Buechler et al. |
| 2008/0071151 A1 | 3/2008 | Sogin et al. |

FOREIGN PATENT DOCUMENTS

| | | |
|---|---|---|
| WO | WO2007028070 A2 | 3/2007 |
| WO | WO2009089286 A1 | 7/2009 |

OTHER PUBLICATIONS

Rudikoff et al. (1982). Single amino acid substitution altering antigen-binding specificity. Proc. Natl. Acad. Sci. USA. 79:1979-1983.*

Belgore F.M., et al., "Measurement of Free and Complexed Soluble Vascular Endothelial Growth Factor Receptor, Flt-1, in Fluid Samples: Development and Application of Two New Immunoassays," Clinical Science, 2001, vol. 100 (5), pp. 567-575.

Brennan M., et al., "Preparation of Bispecific Antibodies by Chemical Recombination of Monoclonal Immunoglobulin G1 Fragments," Science, 1985, vol. 229, pp. 81-83.

Carter P., et al., "High Level *Escherichia Coli* Expression and Production of a Bivalent Humanized Antibody Fragment," Biotechnology, 1992, vol. 10, pp. 163-167.

Cuadros C., et al., "Cooperative Effect Between Immunotherapy and Anti-angiogenic Therapy Leads to Effective Tumour Rejection in Tolerant Her-2/neu Mice," Cancer Research, 2003, vol. 63 (18), pp. 5895-5901.

Hornig C., et al., "Detection and Quantification of Complexed and Free Soluble Human Vascular Endothelial Growth Factor Receptor-1 (sVEGFR-1) by Elisa," Journal of Immunological Methods, 1999, vol. 226 (1-2), pp. 169-177.

International Preliminary Report on Patentability for Application No. PCT/US2009/069342, mailed on Jun. 29, 2011, 7 pages.

International Search Report and Written Opinion for Application No. PCT/US2009/069342, mailed on Apr. 6, 2010, 16 pages.

Janson, et al., "Protein Purification," 1989, vol. 3, pp. 281-283, and 311.

McKeeman G.C., et al., "Soluble Vascular Endothelial Growth Factor Receptor-1 (sFlt-1) is Increased Throughout Gestation in Patients Who Have Preeclampsia Develop," American Journal of Obstetrics and Gynecology, 2004, vol. 191 (4), pp. 1240-1246.

Morimoto K., et al., "Single-Step Purification of F(ab) 2 Fragments of Mouse Monoclonal Antibodies (Immunoglobulins G1) by Hydrophobic Interaction High Performance Liquid Chromatography Using TSKgel Phenyl-5PW," Journal of Biochemical and Biophysical Methods, 1992, vol. 24, pp. 107-117.

Oi V.T., et al., "Chimeric Antibodies," BioTechniques, 1986, vol. 4 (3), pp. 214-221.

(Continued)

*Primary Examiner* — Christine J Saoud
*Assistant Examiner* — Jon M Lockard
(74) *Attorney, Agent, or Firm* — Audrey L. Bartnicki; Carol Larcher; Larcher & Chao Law Group

(57) ABSTRACT

An isolated antibody that specifically binds to sFlt-1 or a fragment thereof having (i) a variable heavy domain region comprising the amino acid sequence of SEQ ID NO: 2, (ii) a variable light domain region comprising the amino acid sequence of SEQ ID NO: 4, or (iii) both (i) and (ii), a pharmaceutical composition and a kit comprising such an antibody, a method of making such an antibody, a method of determining the presence, amount or concentration of sFlt-1 or a fragment thereof in a test sample, a method of treating a patient in therapeutic or prophylactic need of an antagonist of sFlt-1, an isolated nucleic acid comprising a nucleotide sequence encoding the amino acid sequence of (i) SEQ ID NO: 2, (ii) SEQ ID NO: 4, or (iii) both (i) and (ii), optionally as part of a vector, and a host cell comprising and expressing such a nucleic acid.

3 Claims, 7 Drawing Sheets

OTHER PUBLICATIONS

Poljak R.J., "Production and Structure of Diabodies," Structure, 1994, vol. 2 (12), pp. 1121-1123.

Quantikine Human Lipocalin-2/NGAL Immunoassay Catalog No. N20 [online], 2007, [Retrieved on Jul. 4, 2007]. Retrieved from the Internet:< URL:http://www.rndssystems.com/pdf/DLCN20.pdf>.

R&D Systems, Monoclonal Anti-Human VEGF R1 (Flt-1) Antibody, Catalog Number: MAB321, 2008.

Razavi Z., et al., "Stable and Versatile Active Acridinium Esters ll," Luminescence, 2000, vol. 15, pp. 245-249.

Roberts J.M., et al., "Summary of the NHLBI Working Group on Research on Hypertension During Pregancy," Hypertension, 2003, vol. 41 (3), pp. 437-445.

Stewart J.M., et al., Solid-Phase Peptide Synthesis, 2nd Edition, Pierce Chemical Company, 1984, Table of Contents.

Wells D.A., et al., "High Throughput Bioanalytical Sample Preparation Methods and Automation Strategies," Progress in Pharmaceutical and Biomedical Analysis, 2003, pp. 1-23.

\* cited by examiner

```
  1   CAGGTTCAG CTGCAGCAG TCTGGGGCT GAGCTGGTG GGGCCTGGG TCCTCAGTG
      GTCCAAGTC GACGTCGTC AGACCCCGA CTCGACCAC CCCGGACCC AGGAGTCAC

CDR-H1 (10aa)
                                         ~~~~~~~~~~~~~~~~~~~~~~
 55   AAGATTTCC TGCAAGGCT TCTGGCTAT GCATTCAGT AGCTACTGG ATGAACTGG
      TTCTAAAGG ACGTTCCGA AGACCGATA CGTAAGTCA TCGATGACC TACTTGACC

CDR-H2 (17aa)
                                                  ~~~~~~~~~~~~~
109   GTGAAGCAG AGGCCTGGA CAGGGTCTT GAGTGGATT GGACAGATT TATCCTGGA
      CACTTCGTC TCCGGACCT GTCCCAGAA CTCACCTAA CCTGTCTAA ATAGGACCT

CDR-H2 (17aa)
      ~~~~~~~~~~~~~~~~~~~~~~~~~~~~~~~~~~~~~~~~~
163   GATGGTGAT ACTAACTAC AATGGAAAG TTCAGGGGT AAAGTCACA CTGACTGCA
      CTACCACTA TGATTGATG TTACCTTTC AAGTCCCCA TTTCAGTGT GACTGACGT

217   GACAGATCC TCCAGCACA GCCGACATG CAGCTCAGC AGTCTGACA TCTGAGGAC
      CTGTCTAGG AGGTCGTGT CGGCTGTAC GTCGAGTCG TCAGACTGT AGACTCCTG

CDR-H3 (9aa)
                                                  ~~~~~~~~~~~~
271   TCTGCGGTC TATTTCTGT GCAAGAGAT GATGGTTAC GAGGGGTTT GACTACTGG
      AGACGCCAG ATAAAGACA CGTTCTCTA CTACCAATG CTCCCCAAA CTGATGACC

325   GGCCAAGGC ACCACGCTC ACAGTCTCC TCA [SEQ ID NO: 1]
      CCGGTTCCG TGGTGCGAG TGTCAGAGG AGT

1   QVQLQQSGAE LVGPGSSVKI SCKAS<u>GYAFS</u> <u>SYWMN</u>WVKQR PGQGLEWIG<u>Q</u>
 51   <u>IYPGDGDTNY</u> <u>NGKFRG</u>KVTL TADRSSSTAD MQLSSLTSED SAVYFCAR<u>DD</u>
101   <u>GYEGFD</u>YWGQ GTTLTVSS [SEQ ID NO: 2]
```

Fig. 1

```
  1  GACATTGTG ATGACCCAG TCTCAAAAA TTCATGTCC ACAACAGTA GGAGACAGG
     CTGTAACAC TACTGGGTC AGAGTTTTT AAGTACAGG TGTTGTCAT CCTCTGTCC

CDR-L1 (11aa)
                       ~~~~~~~~~~~~~~~~~~~~~~~~~~~~~~~~~
 55  GTCAGCCTC ACCTGCAAG GCCAGTCAG AGTGTGGGG ACTGCTGTA GCCTGGTAT
     CAGTCGGAG TGGACGTTC CGGTCAGTC TCACACCCC TGACGACAT CGGACCATA

CDR-L2 (7aa)
                                          ~~~~~~~~~~~~~~~~~~~~
109  CAAGAGAAA ACAGGACAA TCTCCTAAA CTACTGATT TACTCAGCA TCCAATCGG
     GTTCTCTTT TGTCCTGTT AGAGGATTT GATGACTAA ATGAGTCGT AGGTTAGCC

CDR-L2 (7aa)
     ~~~~~~
163  TACACTGGA GTCCCTGAT CGCTTCACA GGCAGTGGA TCTGGGACA GATTTCATT
     ATGTGACCT CAGGGACTA GCGAAGTGT CCGTCACCT AGACCCTGT CTAAAGTAA

CDR-L3 (9aa)
                                                       ~~~~~
217  CTCACCATT CGCAATATG CAGTCTGTA GACCTGGCA GATTATTTC TGTCAGCAG
     GAGTGGTAA GCGTTATAC GTCAGACAT CTGGACCGT CTAATAAAG ACAGTCGTC

CDR-L3 (9aa)
     ~~~~~~~~~~~~~~~~~~~
271  TATTTCACC TATCCGTAC ACGTTCGGA GGGGGGACC AAGCTGGAA ATACAACGG
     ATAAAGTGG ATAGGCATG TGCAAGCCT CCCCCCTGG TTCGACCTT TATGTTGCC
     [SEQ ID NO: 3]

1  DIVMTQSQKF MSTTVGDRVS LTC$\underline{KASQSVG}$ $\underline{TAVA}$WYQEKT GQSPKLLIY$\underline{S}$
 51  $\underline{ASNRYT}$GVPD RFTGSGSGTD FILTIRNMQS VDLADYFC$\underline{QQ}$ $\underline{YFTYPYT}$FGG
101  GTKLEIQR [SEQ ID NO: 4]
```

Fig. 2

| mAb on Microparticle | mAb Conjugate | | | | | | | | | | | | | | | | | | | | | | | |
|---|---|---|---|---|---|---|---|---|---|---|---|---|---|---|---|---|---|---|---|---|---|---|---|---|
| | 1-833-527 | 1-330-202 | 1-333-205 | 1-654-302 | 1-738-256 | 1-753-317 | 1-780-103 | 1-1072-134 | 1-1103-336 | 1-1140-422 | 1-2315-140 | 2-106-105 | 2-187-107 | 2-616-106 | 2-617-102 | 2-684-121 | 2-1012-125 | 2-154-307 | 2-1014-365 | BDS MAb 321 | BDS 49508 | BDS 49511 | BDS 49566 | PlGF |
| 1-833-527 | | | 1 | | | | 3 | | | | | 3 | | | | | | | | 3 | 1 | | 3 | 3 |
| 1-330-202 | | | | | | | | | | | | | | | | | | | | | | | | |
| 1-333-205 | 1 | | | | | | | | | | 1 | | | | | | | | | | | | | |
| 1-654-302 | | | | | | | 3 | | | | | | | | | | | | | 3 | 1 | | 3 | 2 |
| 1-738-256 | | | | | 2 | | | | | | | | | | | | | | | 3 | 1 | | 2 | |
| 1-753-317 | | | | | | 2 | 3 | | | | | | | | | | | | | 3 | 1 | | 3 | 2 |
| 1-780-103 | | | | | | | | | | 1 | | | | | | | | | | 2 | 1 | | 2 | 1 |
| 1-1072-134 | | | 1 | | | | 3 | | 3 | 3 | 1 | | | | | | | | | 3 | 1 | | 3 | 2 |
| 1-1103-336 | | | | | | | 3 | | | | | | | | | | | | | 3 | 1 | | 3 | |
| 1-1140-422 | | | | | 2 | 2 | 3 | | | | | | | | | | | | | 3 | 1 | | 3 | 2 |
| 1-2315-140 | | | | | 2 | 2 | | | | | | 2 | 2 | 2 | 2 | 2 | 2 | | 2 | 3 | 1 | | 2 | |
| 2-106-105 | 3 | | | | | | | 3 | 2 | 2 | 3 | | | | | | | | | | | | | |

3 = reacts with sFlt-1 domains 1-3, sFlt-1 domains 1-3:Fc chimera, and sFlt-1 domains 1-6:Fc chimera
2 = reacts with sFlt-1 domains 1-3:Fc chimera and sFlt-1 domains 1-6:Fc chimera
1 = reacts with sFlt-1 domains 1-6:Fc chimera only

Fig. 3A

| mAb on Microparticle \ mAb conjugate | 1-833-527 | 1-330-202 | 1-332-205 | 1-654-303 | 1-238-256 | 1-253-317 | 1-780-103 | 1-1022-134 | 1-1103-336 | 1-1140-422 | 1-2315-140 | 2-106-105 | 2-182-107 | 2-616-106 | 2-612-102 | 2-684-121 | 2-1017-125 | 2-154-307 | 2-1014-365 | RDS Mab 321 | RDS 49508 | RDS 49511 | RDS 49566 | PlGF |
|---|---|---|---|---|---|---|---|---|---|---|---|---|---|---|---|---|---|---|---|---|---|---|---|---|
| 2-187-107 | | | | | | | 1 | | | | | | | | | | | | | 3 | 1 | | 3 | 2 |
| 2-616-106 | | | | | | | 1 | | | | | | | | | | | | | 3 | 1 | | 3 | 2 |
| 2-617-102 | | | | | | | 1 | | | | | | | | | | | | | 3 | 1 | | 3 | 2 |
| 2-684-121 | | | | | | 3 | | 3 | 3 | 3 | 3 | | 3 | 3 | 3 | 3 | 3 | | | 3 | 1 | | 3 | 1 |
| 2-1017-125 | | | | | | 3 | | 3 | 3 | 3 | 3 | | 3 | 3 | 3 | 3 | 3 | | | 3 | 1 | | 2 | |
| 2-154-307 | | | | | | | | | | | | | | | | | | | | | | | 2 | |
| 2-1014-365 | | | | | | | | | | | | | | | | | | | | 3 | 1 | | 3 | |
| R&D Systems (RDS) Mab 321 | 3 | | | 3 | 3 | 3 | | 3 | 3 | 3 | 3 | | 3 | 3 | 3 | 3 | 3 | | | | | | 3 | |
| RDS 49508 | 1 | | | | | | | | | | | | | | | | | | | 1 | | | | |
| RDS 49511 | 3 | | | 3 | 3 | 3 | | 3 | 3 | 3 | 3 | | 3 | 3 | 3 | 3 | 3 | | | | | | 1 | |
| RDS 49566 | 3 | | | 3 | 3 | 3 | | 3 | 3 | 3 | 3 | | 3 | 3 | 3 | 3 | 3 | | | 3 | | | | |

3 = reacts with sFlt-1 domains 1-3, sFlt-1 domains 1-3:Fc chimera, and sFlt-1 domains 1-6:Fc chimera  
2 = reacts with sFlt-1 domains 1-3:Fc chimera and sFlt-1 domains 1-6:Fc chimera  
1 = reacts with sFlt-1 domains 1-6:Fc chimera only

Fig. 3B

SEQUENCE LISTING

<160> NUMBER OF SEQ ID NOS: 9

<210> SEQ ID NO 1
<211> LENGTH: 354
<212> TYPE: DNA
<213> ORGANISM: Artificial
<220> FEATURE:
<223> OTHER INFORMATION: Synthetic

<400> SEQUENCE: 1
caggttcagc tgcagcagtc tggggctgag ctggtggggc ctgggtcctc agtgaagatt      60
tcctgcaagg cttctggcta tgcattcagt agctactgga tgaactgggt gaagcagagg     120
cctggacagg gtcttgagtg gattggacag atttatcctg agatggtga tactaactac     180 aatgaaagt tcagggtaa agtcacactg actgcagaca gatcctccag cacagccgac      240
atgcagctca gcagtctgac atctgaggac tctgcggtct atttctgtgc aagagatgat     300
ggttacgagg ggtttgacta ctggggccaa ggcaccacgc tcacagtctc ctca           354

<210> SEQ ID NO 2
<211> LENGTH: 118
<212> TYPE: PRT
<213> ORGANISM: Artificial
<220> FEATURE:
<223> OTHER INFORMATION: Synthetic

<400> SEQUENCE: 2

Gln Val Gln Leu Gln Gln Ser Gly Ala Glu Leu Val Gly Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Arg Gly Lys Val Thr Leu Thr Ala Asp Arg Ser Ser Ser Thr Ala Asp
65                  70                  75                  80

Met Gln Leu Ser Ser Leu Thr Ser Glu Asp Ser Ala Val Tyr Phe Cys
                85                  90                  95

Ala Arg Asp Asp Gly Tyr Glu Gly Phe Asp Tyr Trp Gly Gln Gly Thr
            100                 105                 110

Thr Leu Thr Val Ser Ser
        115

<210> SEQ ID NO 3
<211> LENGTH: 324
<212> TYPE: DNA
<213> ORGANISM: Artificial
<220> FEATURE:
<223> OTHER INFORMATION: Synthetic

<400> SEQUENCE: 3
gacattgtga tgacccagtc tcaaaaattc atgtccacaa cagtaggaga cagggtcagc      60
ctcacctgca aggccagtca gagtgtgggg actgctgtag cctggtatca agagaaaaca     120
ggacaatctc ctaaactact gatttactca gcatccaatc ggtacactgg agtccctgat     180
cgcttcacag gcagtggatc tgggacagat ttcattctca ccattcgcaa tatgcagtct     240
gtagacctgg cagattattt ctgtcagcag tatttcacct atccgtacac gttcggaggg     300

```
gggaccaagc tggaaataca acgg                                              324
```

<210> SEQ ID NO 4
<211> LENGTH: 108
<212> TYPE: PRT
<213> ORGANISM: Artificial
<220> FEATURE:
<223> OTHER INFORMATION: Synthetic

<400> SEQUENCE: 4

```
Asp Ile Val Met Thr Gln Ser Gln Lys Phe Met Ser Thr Thr Val Gly
1               5                   10                  15

Asp Arg Val Ser Leu Thr Cys Lys Ala Ser Gln Ser Val Gly Thr Ala
            20                  25                  30

Val Ala Trp Tyr Gln Glu Lys Thr Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Ile Leu Thr Ile Arg Asn Met Gln Ser
65                  70                  75                  80

Val Asp Leu Ala Asp Tyr Phe Cys Gln Gln Tyr Phe Thr Tyr Pro Tyr
                85                  90                  95

Thr Phe Gly Gly Gly Thr Lys Leu Glu Ile Gln Arg
            100                 105
```

<210> SEQ ID NO 5
<211> LENGTH: 2651
<212> TYPE: DNA
<213> ORGANISM: Homo sapien
<220> FEATURE:
<221> NAME/KEY: CDS
<222> LOCATION: (250)..(2313)

<400> SEQUENCE: 5

```
gcggacactc ctctcggctc ctccccggca gcggcggcgg ctcggagcgg gctccggggc     60
tcgggtgcag cggccagcgg gcctggcggc gaggattacc cggggaagtg gttgtctcct    120
ggctggagcc gcgagacggg cgctcagggc gcggggccgg cggcggcgaa cgagaggacg    180
gactctggcg ccgggtcgt tggccggggg agcgcgggca ccgggcgagc aggccgcgtc     240 gcgctcacc atg gtc agc tac tgg gac acc ggg gtc ctg ctg tgc gcg ctg    291
           Met Val Ser Tyr Trp Asp Thr Gly Val Leu Leu Cys Ala Leu
             1               5                  10 ctc agc tgt ctg ctt ctc aca gga tct agt tca ggt tca aaa tta aaa    339
Leu Ser Cys Leu Leu Leu Thr Gly Ser Ser Ser Gly Ser Lys Leu Lys
15                  20                  25                  30 gat cct gaa ctg agt tta aaa ggc acc cag cac atc atg caa gca ggc    387
Asp Pro Glu Leu Ser Leu Lys Gly Thr Gln His Ile Met Gln Ala Gly
                35                  40                  45 cag aca ctg cat ctc caa tgc agg ggg gaa gca gcc cat aaa tgg tct    435
Gln Thr Leu His Leu Gln Cys Arg Gly Glu Ala Ala His Lys Trp Ser
            50                  55                  60 ttg cct gaa atg gtg agt aag gaa agc gaa agg ctg agc ata act aaa    483
Leu Pro Glu Met Val Ser Lys Glu Ser Glu Arg Leu Ser Ile Thr Lys
        65                  70                  75 tct gcc tgt gga aga aat ggc aaa caa ttc tgc agt act tta acc ttg    531
Ser Ala Cys Gly Arg Asn Gly Lys Gln Phe Cys Ser Thr Leu Thr Leu
    80                  85                  90 aac aca gct caa gca aac cac act ggc ttc tac agc tgc aaa tat cta    579
Asn Thr Ala Gln Ala Asn His Thr Gly Phe Tyr Ser Cys Lys Tyr Leu
95                  100                 105                 110
```

```
gct gta cct act tca aag aag aag gaa aca gaa tct gca atc tat ata    627
Ala Val Pro Thr Ser Lys Lys Lys Glu Thr Glu Ser Ala Ile Tyr Ile
            115             120                 125 ttt att agt gat aca ggt aga cct ttc gta gag atg tac agt gaa atc    675
Phe Ile Ser Asp Thr Gly Arg Pro Phe Val Glu Met Tyr Ser Glu Ile
            130             135                 140 ccc gaa att ata cac atg act gaa gga agg gag ctc gtc att ccc tgc    723
Pro Glu Ile Ile His Met Thr Glu Gly Arg Glu Leu Val Ile Pro Cys
            145             150                 155 cgg gtt acg tca cct aac atc act gtt act tta aaa aag ttt cca ctt    771
Arg Val Thr Ser Pro Asn Ile Thr Val Thr Leu Lys Lys Phe Pro Leu
    160             165             170 gac act ttg atc cct gat gga aaa cgc ata atc tgg gac agt aga aag    819
Asp Thr Leu Ile Pro Asp Gly Lys Arg Ile Ile Trp Asp Ser Arg Lys
175             180             185             190 ggc ttc atc ata tca aat gca acg tac aaa gaa ata ggg ctt ctg acc    867
Gly Phe Ile Ile Ser Asn Ala Thr Tyr Lys Glu Ile Gly Leu Leu Thr
                195             200             205 tgt gaa gca aca gtc aat ggg cat ttg tat aag aca aac tat ctc aca    915
Cys Glu Ala Thr Val Asn Gly His Leu Tyr Lys Thr Asn Tyr Leu Thr
            210             215             220 cat cga caa acc aat aca atc ata gat gtc caa ata agc aca cca cgc    963
His Arg Gln Thr Asn Thr Ile Ile Asp Val Gln Ile Ser Thr Pro Arg
            225             230             235 cca gtc aaa tta ctt aga ggc cat act ctt gtc ctc aat tgt act gct   1011
Pro Val Lys Leu Leu Arg Gly His Thr Leu Val Leu Asn Cys Thr Ala
            240             245             250 acc act ccc ttg aac acg aga gtt caa atg acc tgg agt tac cct gat   1059
Thr Thr Pro Leu Asn Thr Arg Val Gln Met Thr Trp Ser Tyr Pro Asp
255             260             265             270 gaa aaa aat aag aga gct tcc gta agg cga cga att gac caa agc aat   1107
Glu Lys Asn Lys Arg Ala Ser Val Arg Arg Arg Ile Asp Gln Ser Asn
                275             280             285 tcc cat gcc aac ata ttc tac agt gtt ctt act att gac aaa atg cag   1155
Ser His Ala Asn Ile Phe Tyr Ser Val Leu Thr Ile Asp Lys Met Gln
            290             295             300 aac aaa gac aaa gga ctt tat act tgt cgt gta agg agt gga cca tca   1203
Asn Lys Asp Lys Gly Leu Tyr Thr Cys Arg Val Arg Ser Gly Pro Ser
            305             310             315 ttc aaa tct gtt aac acc tca gtg cat ata tat gat aaa gca ttc atc   1251
Phe Lys Ser Val Asn Thr Ser Val His Ile Tyr Asp Lys Ala Phe Ile
            320             325             330 act gtg aaa cat cga aaa cag cag gtg ctt gaa acc gta gct ggc aag   1299
Thr Val Lys His Arg Lys Gln Gln Val Leu Glu Thr Val Ala Gly Lys
335             340             345             350 cgg tct tac cgg ctc tct atg aaa gtg aag gca ttt ccc tcg ccg gaa   1347
Arg Ser Tyr Arg Leu Ser Met Lys Val Lys Ala Phe Pro Ser Pro Glu
                355             360             365 gtt gta tgg tta aaa gat ggg tta cct gcg act gag aaa tct gct cgc   1395
Val Val Trp Leu Lys Asp Gly Leu Pro Ala Thr Glu Lys Ser Ala Arg
            370             375             380 tat ttg act cgt ggc tac tcg tta att atc aag gac gta act gaa gag   1443
Tyr Leu Thr Arg Gly Tyr Ser Leu Ile Ile Lys Asp Val Thr Glu Glu
            385             390             395 gat gca ggg aat tat aca atc ttg ctg agc ata aaa cag tca aat gtg   1491
Asp Ala Gly Asn Tyr Thr Ile Leu Leu Ser Ile Lys Gln Ser Asn Val
            400             405             410 ttt aaa aac ctc act gcc act cta att gtc aat gtg aaa ccc cag att   1539
Phe Lys Asn Leu Thr Ala Thr Leu Ile Val Asn Val Lys Pro Gln Ile
415             420             425             430
```

```
                                         -continued
tac gaa aag gcc gtg tca tcg ttt cca gac ccg gct ctc tac cca ctg    1587
Tyr Glu Lys Ala Val Ser Ser Phe Pro Asp Pro Ala Leu Tyr Pro Leu
            435                 440                 445 ggc agc aga caa atc ctg act tgt acc gca tat ggt atc cct caa cct    1635
Gly Ser Arg Gln Ile Leu Thr Cys Thr Ala Tyr Gly Ile Pro Gln Pro
        450                 455                 460 aca atc aag tgg ttc tgg cac ccc tgt aac cat aat cat tcc gaa gca    1683
Thr Ile Lys Trp Phe Trp His Pro Cys Asn His Asn His Ser Glu Ala
    465                 470                 475 agg tgt gac ttt tgt tcc aat aat gaa gag tcc ttt atc ctg gat gct    1731
Arg Cys Asp Phe Cys Ser Asn Asn Glu Glu Ser Phe Ile Leu Asp Ala
480                 485                 490 gac agc aac atg gga aac aga att gag agc atc act cag cgc atg gca    1779
Asp Ser Asn Met Gly Asn Arg Ile Glu Ser Ile Thr Gln Arg Met Ala
495                 500                 505                 510 ata ata gaa gga aag aat aag atg gct agc acc ttg gtt gtg gct gac    1827
Ile Ile Glu Gly Lys Asn Lys Met Ala Ser Thr Leu Val Val Ala Asp
                515                 520                 525 tct aga att tct gga atc tac att tgc ata gct tcc aat aaa gtt ggg    1875
Ser Arg Ile Ser Gly Ile Tyr Ile Cys Ile Ala Ser Asn Lys Val Gly
            530                 535                 540 act gtg gga aga aac ata agc ttt tat atc aca gat gtg cca aat ggg    1923
Thr Val Gly Arg Asn Ile Ser Phe Tyr Ile Thr Asp Val Pro Asn Gly
        545                 550                 555 ttt cat gtt aac ttg gaa aaa atg ccg acg gaa gga gag gac ctg aaa    1971
Phe His Val Asn Leu Glu Lys Met Pro Thr Glu Gly Glu Asp Leu Lys
    560                 565                 570 ctg tct tgc aca gtt aac aag ttc tta tac aga gac gtt act tgg att    2019
Leu Ser Cys Thr Val Asn Lys Phe Leu Tyr Arg Asp Val Thr Trp Ile
575                 580                 585                 590 tta ctg cgg aca gtt aat aac aga aca atg cac tac agt att agc aag    2067
Leu Leu Arg Thr Val Asn Asn Arg Thr Met His Tyr Ser Ile Ser Lys
                595                 600                 605 caa aaa atg gcc atc act aag gag cac tcc atc act ctt aat ctt acc    2115
Gln Lys Met Ala Ile Thr Lys Glu His Ser Ile Thr Leu Asn Leu Thr
            610                 615                 620 atc atg aat gtt tcc ctg caa gat tca ggc acc tat gcc tgc aga gcc    2163
Ile Met Asn Val Ser Leu Gln Asp Ser Gly Thr Tyr Ala Cys Arg Ala
        625                 630                 635 agg aat gta tac aca ggg gaa gaa atc ctc cag aag aaa gaa att aca    2211
Arg Asn Val Tyr Thr Gly Glu Glu Ile Leu Gln Lys Lys Glu Ile Thr
    640                 645                 650 atc aga ggt gag cac tgc aac aaa aag gct gtt ttc tct cgg atc tcc    2259
Ile Arg Gly Glu His Cys Asn Lys Lys Ala Val Phe Ser Arg Ile Ser
655                 660                 665                 670 aaa ttt aaa agc aca agg aat gat tgt acc aca caa agt aat gta aaa    2307
Lys Phe Lys Ser Thr Arg Asn Asp Cys Thr Thr Gln Ser Asn Val Lys
                675                 680                 685 cat taa aggactcatt aaaaagtaac agttgtctca tatcatcttg atttattgtc    2363
His actgttgcta actttcaggc tcggaggaga tgctcctccc aaaatgagtt cggagatgat    2423
agcagtaata atgagacccc cgggctccag ctctgggccc cccattcagg ccgaggggggc    2483 tgctccgggg ggccgacttg gtgcacgttt ggatttggag gatccctgca ctgccttctc    2543
tgtgtttgtt gctcttgctg ttttctcctg cctgataaac aacaacttgg gatgatcctt    2603
tccattttga tgccaacctc ttttttatttt taagcggcgc cctatagt    2651

<210> SEQ ID NO 6
<211> LENGTH: 687
```

<212> TYPE: PRT
<213> ORGANISM: Homo sapien

<400> SEQUENCE: 6

```
Met Val Ser Tyr Trp Asp Thr Gly Val Leu Leu Cys Ala Leu Leu Ser
1               5                   10                  15

Cys Leu Leu Leu Thr Gly Ser Ser Gly Ser Lys Leu Lys Asp Pro
            20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
370                 375                 380

Thr Arg Gly Tyr Ser Leu Ile Ile Lys Asp Val Thr Glu Glu Asp Ala
385                 390                 395                 400
```

```
Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Gly Glu His Cys Asn Lys Lys Ala Val Phe Ser Arg Ile Ser Lys Phe
            660                 665                 670

Lys Ser Thr Arg Asn Asp Cys Thr Thr Gln Ser Asn Val Lys His
        675                 680                 685

<210> SEQ ID NO 7
<211> LENGTH: 6
<212> TYPE: PRT
<213> ORGANISM: Artificial
<220> FEATURE:
<223> OTHER INFORMATION: Synthetic

<400> SEQUENCE: 7

His His His His His His
1               5

<210> SEQ ID NO 8
<211> LENGTH: 5
<212> TYPE: PRT
<213> ORGANISM: Artificial
<220> FEATURE:
<223> OTHER INFORMATION: Synthetic

<400> SEQUENCE: 8

Asp Asp Asp Asp Lys
1               5
```

```
<210> SEQ ID NO 9
<211> LENGTH: 6
<212> TYPE: PRT
<213> ORGANISM: Artificial
<220> FEATURE:
<223> OTHER INFORMATION: Synthetic

<400> SEQUENCE: 9

Ala Asp Asp Asp Asp Lys
1               5
```

SOLUBLE FMS-LIKE TYROSINE KINASE-1 (SFLT-1) ANTIBODY AND RELATED COMPOSITION, KIT, METHODS OF USING, AND MATERIALS AND METHOD FOR MAKING

CROSS-REFERENCE TO RELATED APPLICATIONS

This application claims the priority of U.S. Provisional Patent Application 61/140,561 filed on Dec. 23, 2008 (pending), incorporated by reference in its entirety.

TECHNICAL FIELD

This disclosure relates to an antibody, an isolated nucleic acid, optionally as part of a vector, a host cell comprising same, a method of making an antibody, a method and a kit for determining the presence, amount or concentration of an analyte in a sample, a pharmaceutical composition comprising an antibody, and a method of using the composition to treat a patient.

BACKGROUND

Preeclampsia is a syndrome of hypertension, edema, and proteinuria. It affects about 5-10% of pregnant women, and results in substantial maternal and fetal morbidity and mortality. Symptoms of preeclampsia typically appear after the 20th week of pregnancy and are usually detected by routine screening of the pregnant woman's blood pressure and urine. Such routine screening methods, however, are ineffective for early diagnosis.

FMS-like tyrosine kinase-1 (Flt-1) is a membrane-spanning tyrosine kinase receptor that is differentially expressed in endothelial cells. It is highly expressed by trophoblast cells, which contribute to the formation of the placenta during pregnancy. Vascular endothelial growth factor (VEGF), which is an endothelial cell-specific mitogen, an angiogenic inducer, and a mediator of vascular permeability, binds as a homodimer to Flt-1. Placental growth factor (PlGF) is a member of the VEGF family that also is involved in development of the placenta. PlGF is expressed by cytotrophoblasts and syncytiotrophoblasts, can induce proliferation, migration, and activation of endothelial cells, and binds as a homodimer to Flt-1. Thus, VEGF and PlGF both contribute to mitogenic activity and angiogenesis during development of the placenta.

sFlt-1 is a soluble form of the Flt-1 receptor, and, thus, is also referred to as soluble VEGF receptor-1. It is a splice variant of the Flt-1 receptor that lacks the transmembrane and cytoplasmic domains of the Flt-1 receptor but contains seven IgG-like domains of the external portion of the receptor Like the Flt-1 receptor, sFlt-1 binds to VEGF and PlGF; however, it does not stimulate mitogenesis of endothelial cells. Rather, sFlt-1 prevents proteins from initiating blood vessel growth. It has been identified as a biomarker for the diagnosis of preeclampsia (see, e.g., McKeeman et al., Amer. J. of Obstetrics and Gynecology 191: 1240-1246 (2004)).

Immunoassays, such as enzyme-linked immunosorbent assays (ELISAs), have been developed to measure free and sFlt-1 complexed with VEGF in fluid samples (see, e.g., Karumanchi et al., U.S. Pat. No. 7,335,362, which issued Feb. 26, 2008, and Belgore et al., Clin. Sci. 100: 567-575 (2001)). There remains a need, however, for new materials, methods, and kits for determining the concentration of sFlt-1 in a test sample, such as in the diagnosis of preeclampsia and cardiovascular disease. There also is a need for new compositions and methods for treatment of a patient in therapeutic or prophylactic need of an antagonist of sFlt-1, such as a patient at risk for or having preeclampsia or a cardiovascular disease. The present disclosure seeks to address such needs. These and other objects and advantages of the present disclosure will become apparent from the detailed description provided herein.

SUMMARY

An isolated antibody that specifically binds to soluble FMS-like tyrosine kinase-1 (sFlt-1) or a fragment thereof is provided. The antibody has (i) a variable heavy domain region comprising the amino acid sequence of SEQ ID NO: 2, (ii) a variable light domain region comprising the amino acid sequence of SEQ ID NO: 4, or (iii) a variable heavy domain region comprising the amino acid sequence of SEQ ID NO: 2 and a variable light domain region comprising the amino acid sequence of SEQ ID NO: 4.

An isolated antibody in one aspect specifically binds to soluble FMS-like tyrosine kinase-1 (sFlt-1) or a fragment thereof and has at last one binding constant selected from the group consisting of an association rate constant ($k_a$) between about $9.0 \times 10^5$ $M^{-1}$ $s^{-1}$ to about $4.0 \times 10^6$ $M^{-1}$ $s^{-1}$, a dissociation rate constant ($k_d$) between about $1.0 \times 10^{-4}$ $s^{-1}$ to about $6.0 \times 10^{-4}$ $s^{-1}$ and an equilibrium dissociation constant ($K_D$) between about $0.5 \times 10^{-10}$ M to about $4.0 \times^{-10}$ M.

A method of determining the presence, amount or concentration of sFlt-1 or a fragment thereof in a test sample is also provided. The method comprises assaying the test sample for sFlt-1 (or a fragment thereof) by an immunoassay employing at least one antibody and at least one detectable label. The method further comprises comparing a signal generated by the detectable label as a direct or indirect indication of the presence, amount or concentration of sFlt-1 (or a fragment thereof) in the test sample to a signal generated as a direct or indirect indication of the presence, amount or concentration of sFlt-1 (or a fragment thereof) in a control or calibrator. The calibrator is optionally part of a series of calibrators in which each of the calibrators differs from the other calibrators in the series by the concentration of sFlt-1 (or a fragment thereof). At least one antibody is an isolated antibody, which specifically binds to sFlt-1 (or a fragment thereof) and which has (i) a variable heavy domain region comprising the amino acid sequence of SEQ ID NO: 2, (ii) a variable light domain region comprising the amino acid sequence of SEQ ID NO: 4, or (iii) a variable heavy domain region comprising the amino acid sequence of SEQ ID NO: 2 and a variable light domain region comprising the amino acid sequence of SEQ ID NO: 4. The method can be adapted for use in an automated system or a semi-automated system.

The method can comprise the following steps: (i) contacting the test sample with at least one capture antibody, which binds to an epitope on sFlt-1 (or a fragment thereof), so as to form a capture antibody/sFlt-1 (or a fragment thereof) complex, (ii) contacting the capture antibody/sFlt-1 (or a fragment thereof) complex with at least one detection antibody, which comprises a detectable label and binds to an epitope on sFlt-1 (or a fragment thereof) that is not bound by the capture antibody, to form a capture antibody/sFlt-1 (or a fragment thereof)/detection antibody complex, and (iii) determining the presence, amount or concentration of sFlt-1 (or a fragment thereof) in the test sample based on the signal generated by the detectable label in the capture antibody/sFlt-1 (or a fragment thereof)/detection antibody complex formed in (ii).

Alternatively, the method can comprise the following steps: (i) contacting the test sample with at least one capture antibody, which binds to an epitope on sFlt-1 (or a fragment thereof) so as to form a capture antibody/sFlt-1 (or a fragment thereof) complex, and simultaneously or sequentially, in either order, contacting the test sample with detectably labeled sFlt-1 (or a fragment thereof), which can compete with any sFlt-1 (or a fragment thereof) in the test sample for binding to the at least one capture antibody, wherein any sFlt-1 (or a fragment thereof) present in the test sample and the detectably labeled sFlt-1 compete with each other to form a capture antibody/sFlt-1 (or a fragment thereof) complex and a capture antibody/detectably labeled sFlt-1 (or a fragment thereof) complex, respectively, and (ii) determining the presence, amount or concentration of sFlt-1 in the test sample based on the signal generated by the detectable label in the capture antibody/detectably labeled sFlt-1 (or a fragment thereof) complex formed in (ii).

The method can further comprise simultaneously or sequentially, in either order, determining the amount or concentration of vascular endothelial growth factor (VEGF) (or a fragment thereof) and/or placental growth factor (PlGF) (or a fragment thereof) in the test sample, which method comprises assaying the test sample for VEGF (or a fragment thereof) and/or PlGF (or a fragment thereof) by an assay employing at least one specific binding partner for VEGF (or a fragment thereof) and/or at least one specific binding partner for PlGF (or a fragment thereof), respectively, and at least one detectable label and comprising comparing a signal generated by the detectable label as a direct or indirect indication of the amount or concentration of VEGF (or a fragment thereof) and/or PlGF (or a fragment thereof) in the test sample to a signal generated as a direct or indirect indication of the concentration of VEGF and/or PlGF, respectively, in a control or calibrator, which is optionally part of a series of calibrators in which each of the calibrators differs from the other calibrators in the series by the amount or concentration of VEGF or PlGF, respectively.

The method can further comprise diagnosing, prognosticating, or assessing the efficacy of therapeutic/prophylactic treatment of a patient from whom the test sample was obtained. If the method further comprises assessing the therapeutic/prophylactic treatment of the patient, the method optionally further comprises modifying the therapeutic/prophylactic treatment of the patient as needed to improve efficacy.

Also provided is a kit for assaying a test sample for sFlt-1 (or a fragment thereof). The kit comprises at least one component for assaying the test sample for sFlt-1 (or a fragment thereof) and instructions for assaying the test sample for sFlt-1 (or a fragment thereof). At least one component includes an isolated antibody that specifically binds to sFlt-1 (or a fragment thereof). The antibody has (i) a variable heavy domain region comprising the amino acid sequence of SEQ ID NO: 2, (ii) a variable light domain region comprising the amino acid sequence of SEQ ID NO: 4, or (iii) a variable heavy domain region comprising the amino acid sequence of SEQ ID NO: 2 and a variable light domain region comprising the amino acid sequence of SEQ ID NO: 4. The antibody is optionally detectably labeled.

A pharmaceutical composition is also provided. The composition comprises a therapeutically or prophylactically effective amount of an isolated antibody that specifically binds to sFlt-1 (or a fragment thereof). The antibody has (i') a variable heavy domain region comprising the amino acid sequence of SEQ ID NO: 2, (ii') a variable light domain region comprising the amino acid sequence of SEQ ID NO: 4, or (iii') a variable heavy domain region comprising the amino acid sequence of SEQ ID NO: 2 and a variable light domain region comprising the amino acid sequence of SEQ ID NO: 4. The composition further comprises a pharmaceutically acceptable carrier, diluent, and/or excipient and, optionally, another active agent and/or an adjuvant. The pharmaceutical composition is optionally part of a kit comprising one or more containers in which the antibody, another active agent and/or the adjuvant can be present in the same or different containers.

Also provided is a method of treating a patient in therapeutic or prophylactic need of an antagonist of sFlt-1. The method comprises administering to the patient a pharmaceutical composition comprising (i) a therapeutically or prophylactically effective amount of an isolated antibody that specifically binds to sFlt-1 or a fragment thereof. The antibody has (i') a variable heavy domain region comprising the amino acid sequence of SEQ ID NO: 2, (ii') a variable light domain region comprising the amino acid sequence of SEQ ID NO: 4, or (iii') a variable heavy domain region comprising the amino acid sequence of SEQ ID NO: 2 and a variable light domain region comprising the amino acid sequence of SEQ ID NO: 4. The composition further comprises a pharmaceutically acceptable carrier, diluent, and/or excipient and, optionally, another active agent and/or an adjuvant.

An isolated nucleic acid is further provided. The nucleic acid comprises a nucleotide sequence encoding the amino acid sequence of (i) SEQ ID NO: 2, (ii) SEQ ID NO: 4, or (iii) SEQ ID NO: 2 and SEQ ID NO: 4, optionally as part of a vector. The nucleic acid can comprise the nucleotide sequence of (i) SEQ ID NO: 1, (ii) SEQ ID NO: 3, or (iii) SEQ ID NO: 1 and SEQ ID NO: 3, optionally as part of a vector.

Still further provided is a host cell. The host cell comprises and expresses an isolated nucleic acid comprising a nucleotide sequence encoding the amino acid sequence of (i) SEQ ID NO: 2, (ii) SEQ ID NO: 4, or (iii) SEQ ID NO: 2 and SEQ ID NO: 4, optionally as part of a vector.

Even still further provided is a method of making an antibody that binds to sFlt-1 or a fragment thereof. The method comprises (i) expressing an isolated nucleic acid comprising a nucleotide sequence encoding the amino acid sequence of (i') SEQ ID NO: 2, (ii') SEQ ID NO: 4, or (iii') SEQ ID NO: 2 and SEQ ID NO: 4 in a host cell, and (ii) isolating the antibody.

BRIEF DESCRIPTION OF THE FIGURES

FIG. 1 sets forth the nucleotide (SEQ ID NO: 1) and amino acid (SEQ ID NO: 2) sequences of the variable heavy chain (VH) regions of the anti-sFlt-1 monoclonal antibody 1-833-527, in which the three heavy (H) complementarity determining regions (CDRs) are labeled as CDR-H1, CDR-H2, and CDR-H3 in the figure sequences corresponding to SEQ ID NO: 1, and are underlined in the lowermost part of this figure, in the sequences corresponding to SEQ ID NO: 2.

FIG. 2 sets forth the nucleotide (SEQ ID NO: 3) and amino acid (SEQ ID NO: 4) sequences of the variable light chain (VL) regions of the anti-sFlt-1 monoclonal antibody 1-833-527, in which the three light (L) CDRs are labeled as CDR-L1, CDR-L2, and CDR-L3 in the figure sequences corresponding to SEQ ID NO: 3, and are underlined in the lowermost part of this figure, in the sequences corresponding to SEQ ID NO: 4.

FIG. 3A-B set forth the data generated in accordance with Example 7.

DETAILED DESCRIPTION

Figure 4:
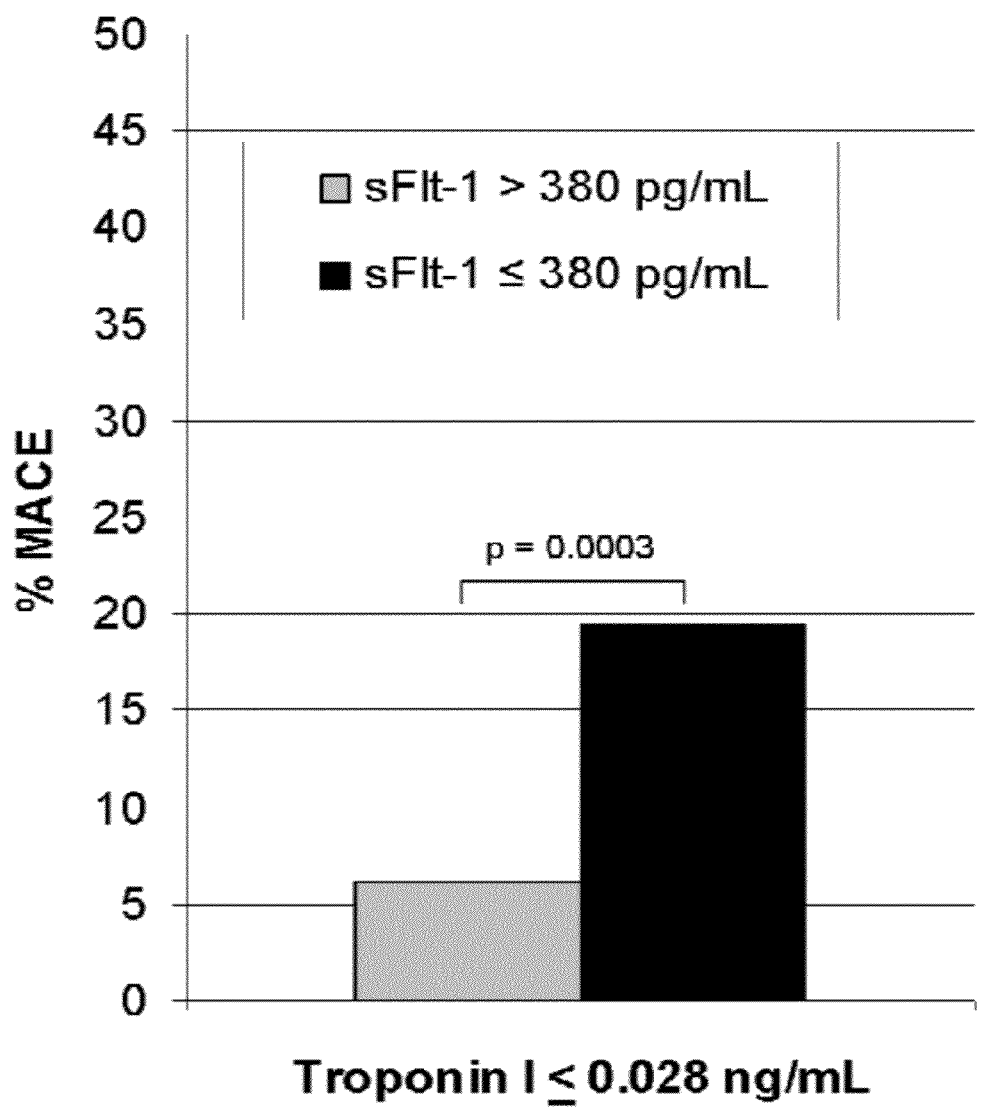
FIG. 4 is a histogram showing risk stratification of Troponin I-negative patients with sFlt-1, as described in Example 11: gray bar, sFlt-1 greater than 380 pg/mL; gray bar, sFlt-1 less than or equal to 380 pg/mL.

The present disclosure is predicated, at least in part, on the discovery of a hybridoma that secretes an anti-soluble FMS-like tyrosine kinase-1 (sFlt-1) antibody. The hybridoma was obtained using refined fusion, cloning and subcloning techniques as exemplified herein to obtain a clonal cell line that can grow in serum-free media earlier in the cell line discovery process. The antibody can bind to sFlt-1, in particular human sFlt-1, within a clinically relevant range of sFlt-1 protein concentration and binds to an epitope that is not bound by known, currently available anti-sFlt-1 monoclonal antibodies. The antibody can be used in an assay, in particular an immunoassay, including the diagnosis, prognosis, and assessment of efficacy of prophylactic/therapeutic treatment of a patient, such as a patient having preeclampsia or a cardiovascular disease, or for assessment of angiogenic activity, among others. The antibody also can be used in a pharmaceutical composition, such as in a method of treating a patient in therapeutic/prophylactic need of an antagonist of sFlt-1.

DEFINITIONS

The following terms are relevant to the present disclosure:

(a) "About" refers to approximately a +/−10% variation from the stated value. It is to be understood that such a variation is always included in any given value provided herein, whether or not specific reference is made to it.

(b) "Antibody" and "antibodies" refer to monoclonal antibodies, multispecific antibodies, human antibodies, humanized antibodies (fully or partially humanized), animal antibodies (such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')$_2$ fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., Nature Biotechnology, 25(11): 1290-1297 (2007) and PCT International Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA and IgY), class (for example, IgG$_1$, IgG$_2$, IgG$_3$, IgG$_4$, IgA$_1$ and IgA$_2$) or subclass. An antibody, whose affinity (namely, $K_D$, $k_d$ or $k_a$) has been increased or improved via the screening of a combinatory antibody library that has been prepared using bio-display, is referred to as an "affinity maturated antibody." For simplicity sake, an antibody against an analyte is frequently referred to herein as being either an "anti-analyte antibody," or merely an "analyte antibody" (e.g., an anti-sFlt-1 antibody or an sFlt-1 antibody).

(c) "Angiogenic activity" or "angiogenesis" refers to the formation of new blood vessels, which plays a role in development, as well as in wound healing, and the transition of tumors from a dormant state to a malignant one (i.e., development of cancer), among other functions.

(d) "Antibody fragment" and "antibody fragments" refer to a portion of an intact antibody comprising the antigen-binding site or variable region. The portion does not include the constant heavy chain domains (i.e., CH2, CH3 or CH4, depending on the antibody isotype) of the Fc region of the intact antibody. Examples of antibody fragments include, but are not limited to, Fab fragments, Fab' fragments, Fab'-SH fragments, F(ab')$_2$ fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region. Such fragments are additionally described above under (b).

(e) "Binding Constants" are as described herein. The term "association rate constant", "$k_{on}$" or "$k_a$" as used interchangeably herein, refers to the value indicating the binding rate of an antibody to its target antigen or the rate of complex formation between an antibody and antigen as shown by the equation below:

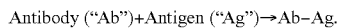

Antibody ("Ab")+Antigen ("Ag")→Ab−Ag.

The term "dissociation rate constant", "$k_{off}$" or "$k_d$" as used interchangeably herein, refers to the value indicating the dissociation rate of an antibody from its target antigen or separation of Ab-Ag complex over time into free antibody and antigen as shown by the equation below:

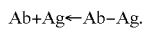

Ab+Ag←Ab−Ag.

Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

The term "equilibrium dissociation constant" or "$K_D$" as used interchangeably, herein, refers to the value obtained by dividing the dissociation rate ($k_{off}$) by the association rate ($k_{on}$). The association rate, the dissociation rate and the equilibrium dissociation constant are used to represent the binding affinity of an antibody to an antigen.

(f) "Bound PlGF" refers to PlGF bound to a VEGF receptor, such as Flt-1 or sFlt-1.

(g) "Bound sFlt-1" refers to sFlt-1 bound to growth factor, such as a vascular endothelial growth factor (VEGF) or placental growth factor (PlGF).

(h) "Bound VEGF" refers to VEGF bound to a VEGF receptor, such as Flt-1 or sFlt-1.

(i) "Cardiovascular disease" refers to various clinical diseases, disorders or conditions involving the heart, blood vessels or circulation. The diseases, disorders or conditions can be due to atherosclerotic impairment of coronary, cerebral or peripheral arteries. Cardiovascular disease includes, but is not limited to, coronary artery disease, peripheral vascular disease, atherosclerosis, hypertension, myocardial infarction (e.g., primary or secondary), angina pectoris, sudden cardiac death, cerebral infarction, restenosis, syncope, ischemia, transient ischemic attack, reperfusion injury, vascular occlusion, carotid obstructive disease, etc. For example, in heart failure, "increased severity" of cardiovascular disease refers to the worsening of disease as indicated by increased NYHA classification, to, for example, Class III or Class IV, and "reduced severity" of cardiovascular disease refers to an improvement of the disease as indicated by reduced NYHA classification, from, for example, class III or IV to class II or I. Cardiovascular disease also can refer to acute coronary syndrome, and major adverse cardiac events (MACE) including but not limited to death, myocardial infarction, or revascularization.

(j) "Component," "components," and "at least one component," refer generally to a capture antibody, a detection or conjugate antibody, a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Some components can be in solution or lyophilized for reconstitution for use in an assay.

(k) "Control" refers to a composition known to not contain sFlt-1 ("negative control") or to contain sFlt-1 ("positive control"). A positive control can comprise a known concentration of sFlt-1. "Control," "positive control," and "calibrator" may be used interchangeably herein to refer to a composition comprising a known concentration of sFlt-1. A "positive control" can be used to establish assay performance characteristics and is a useful indicator of the integrity of reagents (e.g., analytes).

(l) "Eclampsia" refers to severe preeclampsia leading to the development of seizures. It can also include dysfunction or damage to several organs or tissues, such as the liver and central nervous system.

(m) "Epitope," "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

(n) "Free PlGF" refers to PlGF that is not bound to a VEGF receptor, such as Flt-1 or sFlt-1.

(o) "Free sFlt-1" refers to sFlt-1 that is not bound to growth factor.

(p) "Free VEGF" refers to VEGF that is not bound to a VEGF receptor, such as Flt-1 or sFlt-1.

(q) "Heart failure" refers to a condition in which the heart cannot pump blood efficiently to the rest of the body. Heart failure can be due to damage to the heart or narrowing of the arteries due to infarction, cardiomyopathy (primary or secondary), hypertension, coronary artery disease, valve disease, birth defects or infection. Heart failure can further be described as chronic, congestive, acute, decompensated, systolic or diastolic. The New York Heart Association (NYHA) classification describes the severity of the disease based on functional capacity of the patient; NYHA class can progress and/or regress based on treatment or lack of response to treatment.

(r) "Hypertensive disorder of pregnancy (HDP)" is used herein in the context defined by the National Heart, Lung and Blood Institute (NHLBI) (see, e.g., Roberts et al., Hypertension 41(3): 437-445 (2003)). The NHLBI classifies the HDP into 4 categories: (i) Preeclampsia (PE), defined as blood pressure (BP) $\geq$140/90 and >300 mg/24 hours proteinuria at >20 weeks gestation; (ii) Chronic Hypertension (CHTN), defined as BP $\geq$140/90 prior to pregnancy or <20 weeks gestation; (iii) Superimposed preeclampsia on chronic hypertension (PE+CHTN), defined as the development of newly increased proteinuria in a woman with existing chronic hypertension >20 weeks of gestation; and (iv) Gestational Hypertension (GH), defined as hypertension without proteinuria at >20 weeks. Comparison of these measurements with pre-determined values allows the hypertensive status of the subject to be determined, for example, to distinguish between preeclampsia and chronic hypertension.

(s) "Hypertensive status" refers to the condition of a subject with respect to the presence or absence of a hypertensive disorder such as chronic hypertension, HDP, or a hypertensive disorder associated with anti-angiogenic drug therapy.

(t) "Identical" or "identity" as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

(u) "Label" and "detectable label" mean a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromogens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

(v) "Linking sequence" or "linking peptide sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Exemplary linking sequences include, but are not limited to: (i) Histidine (H is) tags, such as a 6×His tag, which has an amino acid sequence of HHHHHH (SEQ ID NO: 7), are useful as linking sequences to facilitate the isolation and purification of polypeptides and antibodies of interest; (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. Examples of enterokinase cleavage sites include, but are not limited to, the amino acid sequence of DDDDK (SEQ ID NO: 8) and derivatives thereof (e.g., ADDDDK (SEQ ID NO: 9), etc.); (iii) Miscellaneous sequences can be used to link or connect the light and/or heavy chain variable regions of single chain variable region fragments. Examples of other linking sequences can be found in Bird et al., Science 242: 423-426 (1988); Huston et al., PNAS USA 85: 5879-5883 (1988); and McCafferty et al., Nature 348: 552-554 (1990). Linking sequences also can be modified for additional functions, such as attachment of drugs or attachment to solid supports. In the context of the present disclosure, the monoclonal antibody, for example, can contain a linking sequence, such as a His tag, an enterokinase cleavage site, or both.

(w) "Patient" and "subject" may be used interchangeably herein to refer to an animal, such as a bird (e.g., a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, and a mouse) and a primate (for example, a monkey, a chimpanzee, and a human). Preferably, the patient or subject is a human, such as a non-pregnant human, a pregnant human, a post-partum human, a human at risk for preeclampsia, a human having preeclampsia, a human at risk for cardiovascular disease, a human having cardiovascular disease, a human with signs and/or symptoms of an acute coronary syndrome, or a human at risk of experiencing a major adverse cardiac event (MACE).

(x) "Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.). The present disclosure provides exemplary predetermined levels. However, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined cutoff/level may vary between assays, the correlations as described herein should be generally applicable.

(y) "Preeclampsia anti-angiogenic index (PAAI)" is equal to [sFlt-1/(VEGF+PlGF)]. A PAAI of greater than 10, in particular greater than 20, is considered to be indicative of preeclampsia or a risk of preeclampsia.

(z) "Preeclampsia" refers to both a multi-system disorder, which is observed during pregnancy and generally occurs after the 20$^{th}$ week of gestation, and is characterized by hypertension with or before the onset of proteinuria and/or other signs of preeclampsia (see below), as well as "preeclampsia-like syndrome" (PLS) associated with anti-angiogenic treatment (e.g., chemotherapy). Other signs can include edema (including brain and liver edema), glomerular dysfunction, and/or coagulation abnormalities. The term "preeclampsia" encompasses the NHLBI HDP designation of "preeclampsia/eclampsia," as well the various clinical forms of the disorder, including mild, moderate, and severe preeclampsia. "Preeclampsia" also includes HELLP syndrome, a variant of severe preeclampsia associated with hemolysis, elevated liver enzyme levels, and low platelet count.

(aa) "Preeclampsia-like syndrome (PLS)" refers to a multi-system disorder that is observed during anti-angiogenic treatment (e.g., chemotherapy), which is characterized by the new onset of hypertension with or without proteinuria, and potentially other symptoms of preeclampsia (see below).

(bb) "Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte (i.e., sFlt-1 or sFlt-1 fragment) entails release of the analyte from any endogenous binding proteins present in the sample. A pretreatment reagent may be homogeneous (not requiring a separation step) or heterogeneous (requiring a separation step). With use of a heterogeneous pretreatment reagent there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

(cc) "Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

(dd) "Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., Nature Biotechnology, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

(ee) "Risk" refers to the possibility or probability of a particular event occurring either presently, or, at some point in the future. "Risk stratification" or "prognosticating the risk" refers to an array of known clinical risk factors that allows physicians to classify patients into a low, moderate, high or highest risk of developing a particular disease, disorder or condition.

(ff) "Sample," "test sample," and "patient sample" may be used interchangeably herein. The sample, such as a sample of urine, serum, plasma, amniotic fluid, cerebrospinal fluid, placental cells or tissue, endothelial cells, leukocytes, or monocytes, can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

(gg) "Series of calibrating compositions" refers to a plurality of compositions comprising a known concentration of sFlt-1, wherein each of the compositions differs from the other compositions in the series by the concentration of sFlt-1.

(hh) "Signs and symptoms of preeclampsia" refers to both patient physical and analytical findings (i.e., signs) and complaints (i.e., symptoms) including hypertension (a systolic blood pressure (BP) greater than 140 mmHg and a diastolic BP greater than 90 mmHg after 20 weeks gestation); new onset proteinuria (1+ by dipstick on urinalysis, greater than 300 mg of protein in a 24-hour urine collection, or random urine protein/creatinine ratio greater than 0.3), and resolution of hypertension and proteinuria by 26 weeks postpartum, or upon cessation of anti-angiogenic therapy. The signs of preeclampsia can also include renal dysfunction, glomerular endotheliosis, edema, neuropathy, coagulopathy and/or fatigue.

(ii) "Solid phase" refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. The solid phase can, for example, be plastic, derivatized plastic, magnetic or non-magnetic metal, glass or silicon, including, for example, a test tube, microtiter well, sheet, bead, microparticle, chip, and other configurations known to those of ordinary skill in the art.

(jj) "Soluble Flt-1 or sFlt-1" refers to the soluble form of the Flt-1 receptor, which is also known as sVEGF-R1, is at least substantially identical or identical to the protein described in GenBank Acc. No. U01134 (SEQ ID NO: 6; nucleotide sequence is SEQ ID NO: 5), and has sFlt-1 biological activity. The biological activity of an sFlt-1 polypeptide can be assayed using various standard methods, e.g., by assaying sFlt-1 binding to VEGF or PlGF. sFlt-1 is used herein to include any sFlt-1 family member or isoform. Degradation products or fragments, such as those that result from the enzymatic cleavage of the Flt-1 receptor (for example, specific metalloproteinases released from the placenta can cleave the extracellular domain of the Flt-1 receptor to release the N-terminal portion of Flt-1 into circulation), are intended to be encompassed by "sFlt-1."

(kk) "Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzymes and enzyme inhibitors, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

(ll) "Specific" and "specificity" in the context of an interaction between members of a specific binding pair (e.g., an antigen (or a fragment thereof) and an antibody (or antigenically reactive fragment thereof)) refer to the selective reactivity of the interaction. The phrase "specifically binds to" and analogous phrases refer to the ability of antibodies (or antigenically reactive fragments thereof) to bind specifically to an antigen, such as s-Flt (or a fragment thereof), and not bind specifically to other antigens (or fragments thereof).

(mm) "Substantially identical" as used herein means that a first sequence and a second sequence are at least from about 50% to about 99% identical over a region from about 8 to about 100 or more residues (including, in particular, any range from about 8 to about 100 residues).

(nn) "Total PlGF" refers to bound PlGF and free PlGF.

(oo) "Total sFlt-1" refers to bound sFlt-1 and free sFlt-1.

(pp) "Total VEGF" refers to bound VEGF and free VEGF.

(qq) "Tracer" means an analyte or analyte fragment conjugated to a label, such as sFlt-1 conjugated to a fluorescein moiety, wherein the analyte conjugated to the label can effectively compete with the analyte for sites on an antibody specific for the analyte.

(rr) "Variant" as used herein means a polypeptide that differs from a given polypeptide (i.e., anti-sFlt-1 antibody) in amino acid sequence by the insertion, deletion, or conservative substitution of amino acids, but that retains the biological activity of the given polypeptide (i.e., can compete with anti-sFlt-1 antibody as defined herein for binding to sFlt-1). A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al., J. Mol. Biol. 157: 105-132 (1982)). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101, which is incorporated herein by reference). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to refer to an antigenically reactive fragment of an anti-sFlt-1 antibody that differs from the corresponding fragment of anti-sFlt-1 antibody in amino acid sequence but is still antigenically reactive and can compete with the corresponding fragment of anti-sFlt-1 antibody for binding with sFlt-1. "Variant" also can be used to describe a polypeptide or a fragment thereof that has been differentially processed, such as by proteolysis, phosphorylation, or other post-translational modification, yet retains its antigen reactivity, i.e., ability to bind to sFlt-1.

The above terminology is provided for the purpose of describing particular embodiments. The terminology is not intended to be limiting.

Anti-sFlt-1 Antibody

An isolated antibody that specifically binds to sFlt-1 or a fragment thereof is provided. The antibody has (i) a variable heavy domain region comprising the amino acid sequence of SEQ ID NO: 2, (ii) a variable light domain region comprising the amino acid sequence of SEQ ID NO: 4, or (iii) a variable heavy domain region comprising the amino acid sequence of SEQ ID NO: 2 and a variable light domain region comprising the amino acid sequence of SEQ ID NO: 4. The antibody binds to human sFlt-1. The antibody also binds to sFlt-1 when it is bound to a VEGF, such as PlGF. Thus, the antibody can be used to determine total sFlt-1 in a test sample in accordance with the methods described herein. However, if the antibody is used in combination with an anti-sFlt-1 antibody that only binds to free sFlt-1, the antibody also can be used to determine free sFlt-1 in a test sample in accordance with the methods described herein. The antibody is preferably used as a capture antibody. The antibody can be employed with other commercially available antibodies, e.g., clone 321 (R&D Systems catalog no. MAB321, alternately referred to herein as "monoclonal antibody 321,").

Synthetic Production

Once sequenced, polypeptides, such as a monoclonal antibody (or a fragment thereof), which specifically binds to sFlt-1, can be synthesized using methods known in the art, such as, for example, exclusive solid phase synthesis, partial solid phase synthesis, fragment condensation, and classical solution synthesis. See, e.g., Merrifield, J. Am. Chem. Soc. 85: 2149 (1963). On solid phase, the synthesis typically begins from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the tradename BIO-BEADS SX-1 by Bio Rad Laboratories (Richmond, Calif.), and the preparation of the hydroxymethyl resin is described by Bodonszky et al., Chem. Ind. (London) 38: 1597 (1966). The benzhydrylamine (BHA) resin has been described by Pietta and Marshall, Chem. Comm. 650 (1970) and is commercially available from Beckman Instruments, Inc. (Palo Alto, Calif.) in the hydrochloride form. Automated peptide synthesizers are commercially available, as are services that make peptides to order.

Thus, the polypeptides can be prepared by coupling an alpha-amino protected amino acid to the chloromethylated resin with the aid of, for example, cesium bicarbonate catalyst, according to the method described by Gisin, Hely. Chim. Acta. 56: 1467 (1973). After the initial coupling, the alpha-amino protecting group is removed by a choice of reagents including trifluoroacetic acid (TFA) or hydrochloric acid (HCl) solutions in organic solvents at room temperature.

Suitable alpha-amino protecting groups include those known to be useful in the art of stepwise synthesis of peptides. Examples of alpha-amino protecting groups are: acyl type protecting groups (e.g., formyl, trifluoroacetyl, and acetyl), aromatic urethane type protecting groups (e.g., benzyloxycarbonyl (Cbz) and substituted Cbz), aliphatic urethane protecting groups (e.g., t-butyloxycarbonyl (Boc), isopropyloxycarbonyl, and cyclohexyloxycarbonyl), and alkyl type protecting groups (e.g., benzyl and triphenylmethyl). Boc and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride and dimethyl formamide (DMF) mixtures.

After the desired amino acid sequence has been completed, the desired peptide is decoupled from the resin support by treatment with a reagent, such as TFA or hydrogen fluoride (HF), which not only cleaves the peptide from the resin, but also cleaves all remaining side chain protecting groups. When the chloromethylated resin is used, HF treatment results in the formation of the free peptide acids. When the benzhydrylamine resin is used, HF treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These and other solid phase peptide synthesis procedures are well-known in the art. Such procedures are also described by Stewart and Young in *Solid Phase Peptide Syntheses* (2nd Ed., Pierce Chemical Company, 1984).

Recombinant Production

A polypeptide, such as a monoclonal antibody (or a fragment thereof), which specifically binds to sFlt-1, can be recombinantly produced using methods known in the art. For example, an isolated nucleic acid comprising a nucleotide sequence encoding the antibody (or a fragment thereof) can be expressed in a host cell, and the antibody can be isolated. The isolated nucleic acid can comprise a nucleotide sequence encoding the amino acid sequence of SEQ ID NO: 2 (VH domain region), such as the nucleotide sequence of SEQ ID NO: 1, and/or a nucleotide sequence encoding the amino acid sequence of SEQ ID NO: 4 (VL domain region), such as the nucleotide sequence of SEQ ID NO: 3. The isolated nucleic acid can be synthesized with an oligonucleotide synthesizer, for example. One of ordinary skill in the art will readily appreciate that, due to the degeneracy of the genetic code, more than one nucleotide sequence can encode a given amino acid sequence. In this regard, a nucleotide sequence encoding an amino acid sequence that is substantially identical to SEQ ID NO: 2 and/or an amino acid sequence that is substantially identical to SEQ ID NO: 4 can be used, provided that the variant antibody as expressed competes with the antibody comprising the amino acid sequence of SEQ ID NO: 2 and/or the amino acid sequence of SEQ ID NO: 4 for the same epitope on sFlt-1. Codons, which are favored by a given host cell, preferably are selected for recombinant production. A nucleotide sequence encoding the amino acid sequence of SEQ ID NO: 2 and/or a nucleotide sequence encoding the amino acid sequence of SEQ ID NO: 4 can be combined with other nucleotide sequences using polymerase chain reaction (PCR), ligation, or ligation chain reaction (LCR) to encode an anti-sFlt-1 antibody or antigenically reactive fragment thereof. The individual oligonucleotides typically contain 5' or 3' overhangs for complementary assembly. Once assembled, the nucleotide sequence encoding an anti-sFlt-1 antibody or antigenically reactive fragment thereof can be inserted into a vector, operably linked to control sequences as necessary for expression in a given host cell, and introduced (such as by transformation or transfection) into a host cell. The nucleotide sequence can be further manipulated (for example, linked to one or more nucleotide sequences encoding additional immunoglobulin domains, such as additional constant regions) and/or expressed in a host cell.

Although not all vectors and expression control sequences may function equally well to express a polynucleotide sequence of interest and not all hosts function equally well with the same expression system, it is believed that those skilled in the art will be able to make a selection among these vectors, expression control sequences, optimized codons, and hosts for use in the present disclosure without any undue experimentation. For example, in selecting a vector, the host must be considered because the vector must be able to replicate in it or be able to integrate into the chromosome. The vector's copy number, the ability to control that copy number, and the expression of any other proteins encoded by the vector, such as antibiotic markers, should also be considered. In selecting an expression control sequence, a variety of factors also can be considered. These include, but are not limited to, the relative strength of the sequence, its controllability, and its compatibility with the nucleotide sequence encoding the anti-sFlt-1 antibody, particularly with regard to potential secondary structures. Hosts should be selected by consideration of their compatibility with the chosen vector, their codon usage, their secretion characteristics, their ability to fold the polypeptide correctly, their fermentation or culture requirements, their ability (or lack thereof) to glycosylate the protein, and the ease of purification of the products encoded by the nucleotide sequence, etc.

The recombinant vector can be an autonomously replicating vector, namely, a vector existing as an extrachromosomal entity, the replication of which is independent of chromosomal replication (such as a plasmid). Alternatively, the vector can be one which, when introduced into a host cell, is integrated into the host cell genome and replicated together with the chromosome(s) into which it has been integrated.

The vector is preferably an expression vector in which the polynucleotide sequence encoding the anti-sFlt-1 antibody is operably linked to additional segments required for transcription of the polynucleotide sequence. The vector is typically derived from plasmid or viral DNA. A number of suitable expression vectors for expression in the host cells mentioned herein are commercially available or described in the literature. Useful expression vectors for eukaryotic hosts, include, but are not limited to, vectors comprising expression control sequences from SV40, bovine papilloma virus, adenovirus and cytomegalovirus. Specific vectors include pcDNA3.1 (+)\Hyg (Invitrogen Corp., Carlsbad, Calif.) and pCI-neo (Stratagene, La Jolla, Calif.). Examples of expression vectors for use in yeast cells include, but are not limited to, the 2μ plasmid and derivatives thereof, the POT1 vector (see, e.g., U.S. Pat. No. 4,931,373), the pJSO37 vector (described in Okkels, Ann. New York Acad. Sci. 782: 202-207 (1996)) and pPICZ A, B or C (Invitrogen). Examples of expression vectors for use in insect cells include, but are not limited to, pVL941, pBG311 (Cate et al., Cell 45: 685-698 (1986)), and pBluebac 4.5 and pMelbac (both of which are available from Invitrogen).

Other vectors that can be used allow the nucleotide sequence encoding the anti-sFlt-1 antibody to be amplified in copy number. Such amplifiable vectors are well-known in the art. These vectors include, but are not limited to, those vectors that can be amplified by dihydrofolate reductase (DHFR) amplification (see, for example, Kaufinan, U.S. Pat. No. 4,470,461; and Kaufinan et al., Mol. Cell. Biol. 2: 1304-1319 (1982)) and glutamine synthetase (GS) amplification (see, for example, U.S. Pat. No. 5,122,464 and European Pat. App. Pub. No. 0 338 841).

The recombinant vector can further comprise a nucleotide sequence enabling the vector to replicate in the host cell in question. An example of such a sequence for use in a mammalian host cell is the SV40 origin of replication. Suitable sequences enabling the vector to replicate in a yeast cell are the yeast plasmid 2μ replication genes REP 1-3 and origin of replication.

The vector can also comprise a selectable marker, namely, a gene or polynucleotide, the product of which complements a defect in the host cell, such as the gene coding for DHFR or the *Schizosaccharomyces pombe* TPI gene (see, e.g., Russell, Gene 40: 125-130 (1985)), or one which confers resistance to a drug, such as ampicillin, kanamycin, tetracycline, chloramphenicol, neomycin, hygromycin or methotrexate. For filamentous fungi, selectable markers include, but are not limited to, amdS, pyrG, arcB, niaD and sC.

Also present in the vector are "control sequences," which are any components that are necessary or advantageous for the expression of the anti-sFlt-1 antibody. Each control sequence can be native or foreign to the nucleotide sequence encoding the anti-sFlt-1 antibody. Such control sequences include, but are not limited to, a leader, a polyadenylation sequence, a propeptide sequence, a promoter, an enhancer or an upstream activating sequence, a signal peptide sequence, and a transcription terminator. At a minimum, the control sequences include at least one promoter operably linked to the polynucleotide sequence encoding the anti-sFlt-1 antibody.

By "operably linked" is meant the covalent joining of two or more nucleotide sequences, by means of enzymatic ligation or otherwise, in a configuration relative to one another such that the normal function of the sequences can be performed. For example, a nucleotide sequence encoding a presequence or secretory leader is operably linked to a nucleotide sequence for a polypeptide if it is expressed as a preprotein that participates in the secretion of the polypeptide; a promoter or enhancer is operably linked to a coding sequence if it affects the transcription of the sequence; a ribosome binding site is operably linked to a coding sequence if it is positioned so as to facilitate translation. Generally, "operably linked" means that the nucleotide sequences being linked are contiguous and, in the case of a secretory leader, contiguous and in the same reading frame. Linking is accomplished by ligation at convenient restriction sites. If such sites do not exist, then synthetic oligonucleotide adaptors or linkers can be used, in conjunction with standard recombinant DNA methods.

A wide variety of expression control sequences can be used in the context of the present disclosure. Such useful expression control sequences include the expression control sequences associated with structural genes of the foregoing expression vectors as well as any sequence known to control the expression of genes of prokaryotic or eukaryotic cells or their viruses, and various combinations thereof. Examples of suitable control sequences for directing transcription in mammalian cells include the early and late promoters of SV40 and adenovirus, for example, the adenovirus 2 major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus E1b region polyadenylation signals and the Kozak consensus sequence (Kozak, J. Mol. Biol. 196: 947-50 (1987)).

In order to improve expression in mammalian cells a synthetic intron can be inserted in the 5' untranslated region of a polynucleotide sequence encoding the antibody or a fragment thereof. An example of a synthetic intron is the synthetic intron from the plasmid pCI-Neo (available from Promega Corporation, Madison, Wis.).

Examples of suitable control sequences for directing transcription in insect cells include, but are not limited to, the polyhedrin promoter, the P10 promoter, the baculovirus immediate early gene 1 promoter, the baculovirus 39K delayed-early gene promoter, and the SV40 polyadenylation sequence.

Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4-c promoter and the inducible GAL promoter.

Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger* α-amylase, *A. niger* or *A. nidulas* glucoamylase, *A. nidulans* acetamidase, *Rhizomucor miehei* aspartic proteinase or lipase, the TPI1 terminator, and the ADH3 terminator.

The polynucleotide sequence encoding the antibody of interest may or may not also include a polynucleotide sequence that encodes a signal peptide. The signal peptide is present when the anti-sFlt-1 antibody is to be secreted from the cells in which it is expressed. Such signal peptide, if present, should be one recognized by the cell chosen for expression of the polypeptide. The signal peptide can be homologous or heterologous to the anti-sFlt-1 monoclonal antibody or can be homologous or heterologous to the host cell, i.e., a signal peptide normally expressed from the host cell or one which is not normally expressed from the host cell. Accordingly, the signal peptide can be prokaryotic, for example, derived from a bacterium, or eukaryotic, for example, derived from a mammalian, insect, filamentous fungal, or yeast cell.

The presence or absence of a signal peptide will, for example, depend on the expression host cell used for the production of the anti-sFlt-1 antibody. For use in filamentous fungi, the signal peptide can conveniently be derived from a gene encoding an *Aspergillus* sp. amylase or glucoamylase, a gene encoding a *Rhizomucor miehei* lipase or protease or a *Humicola lanuginosa* lipase. For use in insect cells, the signal peptide can be derived from an insect gene (see, e.g., Int'l Pat. App. Pub. No. WO 90/05783), such as the lepidopteran *Manduca sexta* adipokinetic hormone precursor (see, e.g., U.S. Pat. No. 5,023,328), the honeybee melittin (Invitrogen), ecdysteroid UDP glucosyltransferase (egt) (Murphy et al., Protein Expression and Purification 4: 349-357 (1993), or human pancreatic lipase (hpl) (Methods in Enzymology 284: 262-272 (1997)).

Specific examples of signal peptides for use in mammalian cells include murine Ig kappa light chain signal peptide (Coloma, J. Imm. Methods 152: 89-104 (1992)). Suitable signal peptides for use in yeast cells include the α-factor signal peptide from *S. cerevisiae* (see, e.g., U.S. Pat. No. 4,870,008), the signal peptide of mouse salivary amylase (see, e.g., Hagenbuchle et al., Nature 289: 643-646 (1981)), a modified carboxypeptidase signal peptide (see, e.g., Valls et al., Cell 48: 887-897 (1987)), the yeast BAR1 signal peptide (see, e.g., Int'l Pat. App. Pub. No. WO 87/02670), and the yeast aspartic protease 3 (YAP3) signal peptide (see, e.g., Egel-Mitani et al., Yeast 6: 127-137 (1990)).

Any suitable host can be used to produce the anti-sFlt-1 antibody, including bacteria, fungi (including yeasts), plant, insect, mammal or other appropriate animal cells or cell lines, as well as transgenic animals or plants. Examples of bacterial host cells include, but are not limited to, gram-positive bacteria, such as strains of *Bacillus*, for example, *B. brevis* or *B. subtilis*, *Pseudomonas* or *Streptomyces*, or gram-negative bacteria, such as strains of *E. coli*. The introduction of a vector into a bacterial host cell can, for instance, be effected by protoplast transformation (see, for example, Chang et al., Molec. Gen. Genet. 168: 111-115 (1979)), using competent cells (see, for example, Young et al., J. of Bacteriology 81: 823-829 (1961), or Dubnau et al., J. of Molec. Biol. 56: 209-221 (1971)), electroporation (see, for example, Shigekawa et al., Biotechniques 6: 742-751 (1988)), or conjugation (see, for example, Koehler et al., J. of Bacteriology 169: 5771-5278 (1987)).

Examples of suitable filamentous fungal host cells include, but are not limited to, strains of *Aspergillus*, for example, *A. oryzae*, *A. niger*, or *A. nidulans*, *Fusarium* or *Trichoderma*. Fungal cells can be transformed by a process involving protoplast formation, transformation of the protoplasts, and regeneration of the cell wall using techniques known to those ordinarily skilled in the art. Suitable procedures for transformation of *Aspergillus* host cells are described in European Pat. App. Pub. No. 238 023 and U.S. Pat. No. 5,679,543. Suitable methods for transforming *Fusarium* species are described by Malardier et al., Gene 78: 147-156 (1989), and Int'l Pat. App. Pub. No. WO 96/00787. Yeast can be transformed using the procedures described by Becker and Guarente, In Abelson, J. N. and Simon, M. I., editors, *Guide to Yeast Genetics and Molecular Biology*, Methods in Enzymology 194: 182-187, Academic Press, Inc., New York; Ito et al, J. of Bacteriology 153:163 (1983); and Hinnen et al., PNAS USA 75: 1920 (1978).

Examples of suitable yeast host cells include strains of *Saccharomyces*, for example, *S. cerevisiae, Schizosaccharomyces, Klyveromyces, Pichia*, such as *P. pastoris* or *P. methanolica, Hansenula*, such as *H. polymorpha* or *yarrowia*. Methods for transforming yeast cells with heterologous polynucleotides and producing heterologous polypeptides therefrom are disclosed by Clontech Laboratories, Inc, Palo Alto, Calif., USA (in the product protocol for the Yeastmaker™ Yeast Tranformation System Kit), and by Reeves et al., FEMS Microbiology Letters 99: 193-198 (1992), Manivasakam et al., Nucleic Acids Research 21: 4414-4415 (1993), and Ganeva et al., FEMS Microbiology Letters 121: 159-164 (1994).

Examples of suitable insect host cells include, but are not limited to, a *Lepidoptora* cell line, such as *Spodoptera frugiperda* (Sf9 or Sf21) or *Trichoplusia ni* cells (High Five) (see, e.g., U.S. Pat. No. 5,077,214). Transformation of insect cells and production of heterologous polypeptides are well-known to those skilled in the art.

Examples of suitable mammalian host cells include Chinese hamster ovary (CHO) cell lines, simian (e.g., Green Monkey) cell lines (COS), mouse cells (for example, NS/O), baby hamster kidney (BHK) cell lines, human cells (such as human embryonic kidney (HEK) cells (e.g., HEK 293 cells (A.T.C.C. Accession No. CRL-1573))), myeloma cells that do not otherwise produce immunoglobulin protein, and plant cells in tissue culture. Preferably, the mammalian host cells are CHO cell lines and HEK 293 cell lines. Another preferred host cell is the B3.2 cell line (e.g., Abbott Laboratories, Abbott Bioresearch Center), or another dihydrofolate reductase deficient (DHFR⁻) CHO cell line (e.g., available from Invitrogen).

Methods for introducing exogenous polynucleotides into mammalian host cells include calcium phosphate-mediated transfection, electroporation, DEAE-dextran mediated transfection, liposome-mediated transfection, viral vectors and the transfection method described by Life Technologies Ltd, Paisley, UK using Lipofectamine™ 2000. These methods are well-known in the art and are described, for example, by Ausbel et al. (eds.), *Current Protocols in Molecular Biology*, John Wiley & Sons, New York, USA (1996). The cultivation of mammalian cells is conducted according to established methods, e.g., as disclosed in Jenkins, Ed., *Animal Cell Biotechnology, Methods and Protocols*, Human Press Inc. Totowa, N.J., USA (1999), and Harrison and Rae, *General Techniques of Cell Culture*, Cambridge University Press (1997).

In the production methods, cells are cultivated in a nutrient medium suitable for production of the anti-sFlt-1 antibody using methods known in the art. For example, cells are cultivated by shake flask cultivation, small-scale or large-scale fermentation (including continuous, batch, fed-batch, or solid state fermentations) in laboratory or industrial fermenters performed in a suitable medium and under conditions allowing the anti-human sFlt-1 monoclonal antibody to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection). If the anti-sFlt-1 antibody is secreted into the nutrient medium, it can be recovered directly from the medium. If the anti-sFlt-1 antibody is not secreted, it can be recovered from cell lysates.

The resulting anti-sFlt-1 antibody can be recovered by methods known in the art. For example, the anti-sFlt-1 antibody can be recovered from the nutrient medium by conventional procedures including, but not limited to, centrifugation, filtration, extraction, spray drying, evaporation, or precipitation.

The anti-sFlt-1 antibody can be purified by a variety of procedures known in the art including, but not limited to, chromatography (such as, but not limited to, ion exchange, affinity, hydrophobic, chromatofocusing, and size exclusion), electrophoretic procedures (such as, but not limited to, preparative isoelectric focusing), differential solubility (such as, but not limited to, ammonium sulfate precipitation), SDS-PAGE, or extraction (see, for example, Janson and Ryden, editors, *Protein Purification*, VCH Publishers, New York (1989)).

Antibody fragments are also contemplated. For example, the antibody fragment can include, but is not limited to, a Fab, a Fab', a Fab'-SH fragment, a di-sulfide linked Fv, a single chain Fv (scFv) and a F(ab')₂ fragment. Various techniques are known to those skilled in the art for the production of antibody fragments. For example, such fragments can be derived via proteolytic digestion of intact antibodies (see, for example, Morimoto et al., J. Biochem. Biophys. Methods 24: 107-117 (1992), and Brennan et al., Science 229: 81 (1985)) or produced directly by recombinant host cells. For example, Fab'-SH fragments can be directly recovered from *E. coli* and chemically coupled to form F(ab')₂ fragments (see, e.g., Carter et al., Bio/Technology 10: 163-167 (1992)). In another embodiment, the F(ab')₂ is formed using the leucine zipper GCN4 to promote assembly of the F(ab')₂ molecule. Alternatively, Fv, Fab or F(ab')₂ fragments can be isolated directly from recombinant host cell culture. Single chain variable region fragments (scFv) are made by linking light and/or heavy chain variable regions by using a short linking peptide or sequence (see, e.g., Bird et al., Science 242: 423-426 (1998)). The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art. Moreover, other forms of single-chain antibodies, such as diabodies are also contemplated by the present disclosure. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see, for example, Holliger et al., PNAS USA 90: 6444-6448 (1993); and Poljak et al., Structure 2: 1121-1123 (1994)).

The antibody and antigenically reactive fragment thereof have a variety of uses. In one aspect, the antibody (or a fragment thereof) can be used as one or more immunodiagnostic reagents. For example, the antibodies of the present disclosure can be used as one or more immunodiagnostic reagents in one or more methods for detecting the presence of sFlt-1 in a test sample. More specifically, the antibody (or antigenically reactive fragment thereof) can be used as a capture antibody or a detection antibody in an immunoassay to detect the presence of sFlt-1, such as human sFlt-1 (or a fragment thereof), in a test sample.

Antibody Production

Other antibodies (or fragments thereof) that specifically bind to sFlt-1 (or a fragment thereof) can be made using a variety of different techniques known in the art. For example, polyclonal and monoclonal antibodies can be raised by immunizing a suitable subject (such as, but not limited to, a rabbit, a goat, a mouse, or other mammal) with an immunogenic preparation, which contains a suitable immunogen. The immunogen can be enriched/purified and isolated from a cell that produces it using affinity chromatography, immune-precipitation or other techniques, which are well-known in the art. Alternatively, immunogen can be prepared using chemical synthesis using routine techniques known in the art (such as, but not limited to, a synthesizer). The antibodies raised in the subject can then be screened to determine if the antibodies bind to the immunogen (or a fragment thereof).

The unit dose of immunogen (namely, the purified protein, tumor cell expressing the protein, or recombinantly expressed immunogen (or a fragment or a variant (or a fragment thereof)

thereof) and the immunization regimen will depend upon the subject to be immunized, its immune status, and the body weight of the subject. To enhance an immune response in the subject, an immunogen can be administered with an adjuvant, such as Freund's complete or incomplete adjuvant.

Immunization of a subject with an immunogen as described above induces a polyclonal antibody response. The antibody titer in the immunized subject can be monitored over time by standard techniques such as an ELISA using an immobilized antigen.

Other methods of raising antibodies include using transgenic mice, which express human immunoglobin genes (see, for example, Int'l Pat. App. Pub. Nos. WO 91/00906, WO 91/10741, and WO 92/03918). Alternatively, human monoclonal antibodies can be produced by introducing an antigen into immune-deficient mice that have been engrafted with human antibody-producing cells or tissues (for example, human bone marrow cells, peripheral blood lymphocytes (PBL), human fetal lymph node tissue, or hematopoietic stem cells). Such methods include raising antibodies in SCID-hu mice (see, for example, Int'l Pat. App. Pub. No. WO 93/05796; U.S. Pat. No. 5,411,749; or McCune et al., Science 241: 1632-1639 (1988)) or Rag-1/Rag-2 deficient mice. Human antibody-immune deficient mice are also commercially available. For example, Rag-2 deficient mice are available from Taconic Farms (Germantown, N.Y.).

Monoclonal antibodies can be generated by immunizing a subject with an immunogen. At the appropriate time after immunization, for example, when the antibody titers are at a sufficiently high level, antibody-producing cells can be harvested from an immunized animal and used to prepare monoclonal antibodies using standard techniques. For example, the antibody-producing cells can be fused by standard somatic cell fusion procedures with immortalizing cells, such as myeloma cells, to yield hybridoma cells. Such techniques are well-known in the art, and include, for example, the hybridoma technique as originally developed by Kohler and Milstein, Nature 256: 495-497 (1975)), the human B cell hybridoma technique (Kozbar et al., Immunology Today 4:72 (1983)), and the Epstein-Barr virus (EBV)-hybridoma technique to produce human monoclonal antibodies (Cole et al., *Monoclonal Antibodies and Cancer Therapy*, Alan R. Liss, Inc. pp. 77-96 (1985)). The technology for producing monoclonal antibody hybridomas is well-known to those skilled in the art.

Monoclonal antibodies also can be made by harvesting antibody-producing cells, for example, splenocytes, from transgenic mice, which express human immunoglobulin genes and which have been immunized with the immunogen. The splenocytes can be immortalized through fusion with human myelomas or through transformation with EBV. These hybridomas can be made using human B cell- or EBV-hybridoma techniques described in the art (See, for example, Boyle et al., European Pat. Pub. No. 0 614 984).

Hybridoma cells producing a monoclonal antibody, which specifically binds to the immunogen, are detected by screening the hybridoma culture supernatants by, for example, screening to select antibodies that specifically bind to the immobilized immunogen (or a fragment thereof), or by testing the antibodies as described herein to determine if the antibodies have the desired characteristics, namely, the ability to bind to immunogen (or a fragment thereof). After hybridoma cells are identified that produce antibodies of the desired specificity, the clones may be subcloned, e.g., by limiting dilution procedures, for example the procedure described by Wands et al. (Gastroenterology 80: 225-232 (1981)), and grown by standard methods.

Hybridoma cells that produce monoclonal antibodies that test positive in the screening assays described herein can be cultured in a nutrient medium under conditions and for a time sufficient to allow the hybridoma cells to secrete the monoclonal antibodies into the culture medium, to thereby produce whole antibodies. Tissue culture techniques and culture media suitable for hybridoma cells are generally described in the art (See, for example, R. H. Kenneth, in *Monoclonal Antibodies: A New Dimension In Biological Analyses*, Plenum Publishing Corp., New York, N.Y. (1980)). Conditioned hybridoma culture supernatant containing the antibody can then be collected. The monoclonal antibodies secreted by the subclones optionally can be isolated from the culture medium by conventional immunoglobulin purification procedures such as, for example, protein A chromatography, hydroxylapatite chromatography, gel electrophoresis, dialysis, or affinity chromatography.

Monoclonal antibodies can be engineered by constructing a recombinant combinatorial immunoglobulin library and screening the library with the immunogen or a fragment thereof. Kits for generating and screening phage display libraries are commercially available (See, for example, the Pharmacia Recombinant Phage Antibody System, Catalog No. 27-9400-01; and the Stratagene SurfZAP Phage Display Kit, Catalog No. 240612). Likewise, yeast display vectors are known in the art and are commercially available (for example, pYD1 available from Invitrogen). Briefly, the antibody library is screened to identify and isolate phages or yeast cells that express an antibody that specifically binds to the immunogen or a fragment thereof. Preferably, the primary screening of the library involves screening with an immobilized immunogen or a fragment thereof.

Following screening, the display phage or yeast is isolated and the polynucleotide encoding the selected antibody can be recovered from the display phage or yeast (for example, from the phage or yeast genome) and subcloned into other expression vectors (e.g., into *Saccharomyces cerevesiae* cells, for example EBY100 cells (Invitrogen)) by well-known recombinant DNA techniques. The polynucleotide can be further manipulated (for example, linked to nucleic acid encoding additional immunoglobulin domains, such as additional constant regions) and/or expressed in a host cell.

Once a monoclonal antibody that specifically binds to sFlt-1 is obtained in accordance with methods described above, it can be sequenced in accordance with methods known in the art. The antibody then can be made using recombinant DNA technology, chemical synthesis, or a combination of chemical synthesis and recombinant DNA technology as described above.

Furthermore, in some aspects of the disclosure, it may be possible to employ commercially available anti-sFlt-1 antibodies or methods for production of anti-sFlt-1 antibodies as described in the literature. These include, but are not limited to, those available from Santa Cruz Biotechnology, Inc. (Santa Cruz, Calif.) and R&D Systems (Minneapolis, Minn.).
Kit A kit for assaying a test sample for sFlt-1 (or a fragment thereof) is also provided. The kit comprises at least one component for assaying the test sample for sFlt-1 and instructions for assaying the test sample for sFlt-1 (or a fragment thereof). The at least one component includes at least one composition comprising an isolated antibody that specifically binds to sFlt-1 (or a fragment thereof). The antibody has (i) a variable heavy domain region comprising the amino acid sequence of SEQ ID NO: 2, (ii) a variable light domain region comprising the amino acid sequence of SEQ ID NO: 4, or (iii) a variable heavy domain region comprising the amino acid sequence of SEQ ID NO: 2 and a variable light domain region comprising the amino acid sequence of SEQ ID NO: 4. The antibody is optionally detectably labeled.

For example, the kit can comprise instructions for assaying the test sample for sFlt-1 (or a fragment thereof) by immunoassay, e.g., chemiluminescent microparticle immunoassay. The instructions can be in paper form or computer-readable form, such as a disk, CD, DVD, or the like. The antibody can be an sFlt-1 capture antibody and/or an sFlt-1 detection antibody. Alternatively or additionally, the kit can comprise a calibrator or control, e.g., purified, and optionally lyophilized, sFlt-1 (or a fragment thereof), and/or at least one container (e.g., tube, microtiter plates or strips, which can be already coated with an anti-sFlt-1 monoclonal antibody) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions also can include instructions for generating a standard curve or a reference standard for purposes of quantifying sFlt-1.

Any antibodies, which are provided in the kit, such as recombinant antibodies specific for sFlt-1, can incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes or reagents for detecting the analyte. The antibodies, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. If desired, the kit can contain a solid phase, such as a magnetic particle, bead, test tube, microtiter plate, cuvette, membrane, scaffolding molecule, film, filter paper, disc or chip.

Method of Determining the Presence, Amount or Concentration of sFlt-1 (or a fragment thereof) in a Test Sample The present disclosure provides a method for determining the presence, amount or concentration of sFlt-1 (or a fragment thereof) in a test sample. Any suitable assay as is known in the art can be used in the method. Examples include, but are not limited to, immunoassay, such as sandwich immunoassay (e.g., monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)), competitive inhibition immunoassay (e.g., forward and reverse), fluorescence polarization immunoassay (FPIA), enzyme multiplied immunoassay technique (EMIT), bioluminescence resonance energy transfer (BRET), and homogeneous chemiluminescent assay, etc. In a SELDI-based immunoassay, a capture reagent that specifically binds sFlt-1 (or a fragment thereof) of interest is attached to the surface of a mass spectrometry probe, such as a pre-activated protein chip array. The sFlt-1 (or a fragment thereof) is then specifically captured on the biochip, and the captured sFlt-1 (or a fragment thereof) is detected by mass spectrometry. Alternatively, the sFlt-1 (or a fragment thereof) can be eluted from the capture reagent and detected by traditional MALDI (matrix-assisted laser desorption/ionization) or by SELDI. A chemiluminescent microparticle immunoassay, in particular one employing the ARCHITECT® automated analyzer (Abbott Laboratories, Abbott Park, Ill.), is an example of a preferred immunoassay.

Methods well-known in the art for collecting, handling and processing urine, blood, serum and plasma, and other body fluids, are used in the practice of the present disclosure, for instance, when the antibodies according to the present disclosure are employed as immunodiagnostic reagents, and/or in an sFlt-1 immunoassay kit. The test sample can comprise further moieties in addition to the sFlt-1 analyte of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary (e.g., most urine samples), pretreatment optionally can be done for mere convenience (e.g., as part of a regimen on a commercial platform).

The pretreatment reagent can be any reagent appropriate for use with the immunoassay and kits of the invention. The pretreatment optionally comprises: (a) one or more solvents (e.g., methanol and ethylene glycol) and salt, (b) one or more solvents, salt and detergent, (c) detergent, or (d) detergent and salt. Pretreatment reagents are known in the art, and such pretreatment can be employed, e.g., as used for assays on Abbott TDx, AxSYM®, and ARCHITECT® analyzers (Abbott Laboratories, Abbott Park, Ill.), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay: Comparison with TDx Monoclonal Whole Blood and EMIT Cyclosporine Assays, Clin. Chem. 45: 432-435 (1999)), and/or as commercially available. Additionally, pretreatment can be done as described in Abbott's U.S. Pat. No. 5,135,875, European Pat. Pub. No. 0 471 293, U.S. Provisional Pat. App. 60/878,017, filed Dec. 29, 2006, and U.S. Pat. App. Pub. No. 2008/0020401 (incorporated by reference in its entirety for its teachings regarding pretreatment). The pretreatment reagent can be a heterogeneous agent or a homogeneous agent.

With use of a heterogeneous pretreatment reagent, the pretreatment reagent precipitates analyte binding protein (e.g., protein that can bind to sFlt-1 or a fragment thereof) present in the sample. Such a pretreatment step comprises removing any analyte binding protein by separating from the precipitated analyte binding protein the supernatant of the mixture formed by addition of the pretreatment agent to sample. In such an assay, the supernatant of the mixture absent any binding protein is used in the assay, proceeding directly to the antibody capture step.

With use of a homogeneous pretreatment reagent there is no such separation step. The entire mixture of test sample and pretreatment reagent are contacted with a labeled specific binding partner for sFlt-1 (or a fragment thereof), such as a labeled anti-sFlt-1 monoclonal antibody (or an antigenically reactive fragment thereof). The pretreatment reagent employed for such an assay typically is diluted in the pretreated test sample mixture, either before or during capture by the first specific binding partner. Despite such dilution, a certain amount of the pretreatment reagent (for example, 5 M methanol and/or 0.6 M ethylene glycol) is still present (or remains) in the test sample mixture during capture.

In a heterogeneous format, after the test sample is obtained from a subject, a first mixture is prepared. The mixture contains the test sample being assessed for sFlt-1 (or fragments thereof) and a first specific binding partner, wherein the first specific binding partner and any sFlt-1 contained in the test sample form a first specific binding partner-sFlt-1 complex. Preferably, the first specific binding partner is an anti-sFlt-1 antibody or a fragment thereof. The order in which the test sample and the first specific binding partner are added to form the mixture is not critical. Preferably, the first specific binding partner is immobilized on a solid phase. The solid phase used in the immunoassay (for the first specific binding partner and, optionally, the second specific binding partner) can be any solid phase known in the art, such as, but not limited to, a magnetic particle, a bead, a test tube, a microtiter plate, a cuvette, a membrane, a scaffolding molecule, a film, a filter paper, a disc and a chip.

After the mixture containing the first specific binding partner-sFlt-1 complex is formed, any unbound sFlt-1 is removed from the complex using any technique known in the art. For example, the unbound sFlt-1 can be removed by washing. Desirably, however, the first specific binding partner is present in excess of any sFlt-1 present in the test sample, such that all sFlt-1 that is present in the test sample is bound by the first specific binding partner.

After any unbound sFlt-1 is removed, a second specific binding partner is added to the mixture to form a first specific binding partner-sFlt-1-second specific binding partner complex. The second specific binding partner is preferably an anti-sFlt-1 antibody that binds to an epitope on sFlt-1 that differs from the epitope on sFlt-1 bound by the first specific binding partner. Moreover, also preferably, the second specific binding partner is labeled with or contains a detectable label as described above.

Any suitable detectable label as is known in the art can be used. For example, the detectable label can be a radioactive label (such as $^3$H, $^{125}$I, $^{35}$S, $^{14}$C, $^{32}$P, and $^{33}$P), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, 2$^{nd}$ ed., Springer Verlag, N.Y. (1997), and in Haugland, *Handbook of Fluorescent Probes and Research Chemicals* (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

A preferred acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In *Luminescence Biotechnology: Instruments and Applications*; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543,524 and 5,783,699 (each of which is incorporated herein by reference in its entirety for its teachings regarding same).

Another preferred acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, *High Throughput Bioanalytical Sample Preparation. Methods and Automation Strategies*, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007. Acridinium-9-carboxylate aryl esters can be dissolved in any suitable solvent, such as degassed anhydrous N,N-dimethylformamide (DMF) or aqueous sodium cholate.

Chemiluminescent assays can be performed in accordance with the methods described in Adamczyk et al., Anal. Chim. Acta 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and the specific binding partner(s) are added to form the mixture for chemiluminescent assay is not critical. If the first specific binding partner is detectably labeled with an acridinium compound, detectably labeled first specific binding partner-sFlt-1 complexes form. Alternatively, if a second specific binding partner is used and the second specific binding partner is detectably labeled with an acridinium compound, detectably labeled first specific binding partner-sFlt-1-second specific binding partner complexes form. Any unbound specific binding partner, whether labeled or unlabeled, can be removed from the mixture using any technique known in the art, such as washing.

Hydrogen peroxide can be generated in situ in the mixture or provided or supplied to the mixture before, simultaneously with, or after the addition of an above-described acridinium compound. Hydrogen peroxide can be generated in situ in a number of ways such as would be apparent to one skilled in the art.

Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Upon the simultaneous or subsequent addition of at least one basic solution to the sample, a detectable signal, namely, a chemiluminescent signal, indicative of the presence of sFlt-1 is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of sFlt-1 in the sample can be quantified. Specifically, the amount of sFlt-1 in the sample is proportional to the intensity of the signal generated. The amount of sFlt-1 present can be quantified by comparing the amount of light generated to a standard curve for sFlt-1 or by comparison to a reference standard. The standard curve can be generated using serial dilutions or solutions of known concentrations of sFlt-1 by mass spectroscopy, gravimetric methods, and other techniques known in the art.

sFlt-1 immunoassays generally can be conducted using any format known in the art, such as, but not limited to, a sandwich format, as further described in U.S. Provisional Patent Application No. 60/981,473 (the '473 application), which was filed on Oct. 19, 2007, and which is hereby incorporated by reference. Specifically, in one format at least two antibodies are employed to separate and quantify sFlt-1, such as human sFlt-1, or a fragment thereof in a sample. More specifically, the at least two antibodies bind to certain different epitopes on sFlt-1 (or a fragment thereof) forming an immune complex, which is referred to as a "sandwich." Generally, in the immunoassays one or more antibodies can be used to capture the sFlt-1 (or a fragment thereof) in the test sample (these antibodies are frequently referred to as a "capture" antibody or "capture" antibodies) and one or more antibodies can be used to bind a detectable (namely, quantifiable) label to the sandwich (these antibodies are frequently referred to as the "detection antibody," the "detection antibodies," the "conjugate," or the "conjugates").

Generally speaking, a sample being tested for (for example, suspected of containing)sFlt-1 (or a fragment thereof) can be contacted with at least one capture antibody (or antibodies) and at least one detection antibody (which can be a second detection antibody or a third detection antibody) either simultaneously or sequentially and in any order. For example, the test sample can be first contacted with at least one capture antibody and then (sequentially) with at least one detection antibody. Alternatively, the test sample can be first contacted with at least one detection antibody and then (sequentially) with at least one capture antibody. In yet another alternative, the test sample can be contacted simultaneously with a capture antibody and a detection antibody.

In the sandwich assay format, a sample suspected of containing sFlt-1 (or a fragment thereof) is first brought into contact with an at least one first capture antibody under conditions that allow the formation of a first antibody/sFlt-1 complex. If more than one capture antibody is used, a first multiple capture antibody/sFlt-1 complex is formed. In a sandwich assay, the antibodies, preferably, the at least one capture antibody, are used in molar excess amounts of the maximum amount of sFlt-1 (or a fragment thereof) expected in the test sample. For example, from about 5 μg to about 1 mg of antibody per mL of buffer (e.g., microparticle coating buffer) can be used.

Competitive inhibition immunoassays, which are often used to measure small analytes because binding by only one antibody is required, comprise sequential and classic formats. In a sequential competitive inhibition immunoassay a capture monoclonal antibody to an analyte of interest is coated onto a well of a microtiter plate. When the sample containing the analyte of interest is added to the well, the analyte of interest binds to the capture monoclonal antibody. After washing, a known amount of labeled (e.g., biotin or horseradish peroxidase (HRP)) analyte is added to the well. A substrate for an enzymatic label is necessary to generate a signal. An example of a suitable substrate for HRP is 3,3',5,5'-tetramethylbenzidine (TMB). After washing, the signal generated by the labeled analyte is measured and is inversely proportional to the amount of analyte in the sample. In a classic competitive inhibition immunoassay a monoclonal antibody to an analyte of interest is coated onto a well of a microtiter plate. However, unlike the sequential competitive inhibition immunoassay, the sample and the labeled analyte are added to the well at the same. Any analyte in the sample competes with labeled analyte for binding to the capture monoclonal antibody. After washing, the signal generated by the labeled analyte is measured and is inversely proportional to the amount of analyte in the sample.

Optionally, prior to contacting the test sample with the at least one capture antibody (for example, the first capture antibody), the at least one capture antibody can be bound to a solid support, which facilitates the separation of the first antibody/sFlt-1 (or a fragment thereof) complex from the test sample. The substrate to which the capture antibody is bound can be any suitable solid support or solid phase that facilitates separation of the capture antibody-analyte complex from the sample. Examples include a well of a plate, such as a microtiter plate, a test tube, a porous gel (e.g., silica gel, agarose, dextran, or gelatin), a polymeric film (e.g., polyacrylamide), beads (e.g., polystyrene beads or magnetic beads), a strip of a filter/membrane (e.g., nitrocellulose or nylon), microparticles (e.g., latex particles, magnetizable microparticles (e.g., microparticles having ferric oxide or chromium oxide cores and homo- or hetero-polymeric coats and radii of about 1-10 microns). The substrate can comprise a suitable porous material with a suitable surface affinity to bind antigens and sufficient porosity to allow access by detection antibodies. A microporous material is generally preferred, although a gelatinous material in a hydrated state can be used. Such porous substrates are preferably in the form of sheets having a thickness of about 0.01 to about 0.5 mm, preferably about 0.1 mm. While the pore size may vary quite a bit, preferably the pore size is from about 0.025 to about 15 microns, more preferably from about 0.15 to about 15 microns. The surface of such substrates can be activated by chemical processes that cause covalent linkage of an antibody to the substrate. Irreversible binding, generally by adsorption through hydrophobic forces, of the antigen or the antibody to the substrate results; alternatively, a chemical coupling agent or other means can be used to bind covalently the antibody to the substrate, provided that such binding does not interfere with the ability of the antibody to bind to sFlt-1.

Alternatively, the antibody can be bound with microparticles, which have been previously coated with streptavidin or biotin (e.g., using Power-Bind™-SA-MP streptavidin-coated microparticles (Seradyn, Indianapolis, Ind.)) or anti-species-specific monoclonal antibodies. If necessary, the substrate can be derivatized to allow reactivity with various functional groups on the antibody. Such derivatization requires the use of certain coupling agents, examples of which include, but are not limited to, maleic anhydride, N-hydroxysuccinimide, and 1-ethyl-3-(3-dimethylaminopropyl) carbodiimide. If desired, one or more capture reagents, such as antibodies (or fragments thereof), each of which is specific for sFlt-1 can be attached to solid phases in different physical or addressable locations (e.g., such as in a biochip configuration (see, e.g., U.S. Pat. No. 6,225,047, Int'l Pat. App. Pub. No. WO 99/51773; U.S. Pat. No. 6,329,209; Intl Pat. App. Pub. No. WO 00/56934, and U.S. Pat. No. 5,242,828). If the capture reagent is attached to a mass spectrometry probe as the solid support, the amount of sFlt-1 bound to the probe can be detected by laser desorptionionization mass spectrometry. Alternatively, a single column can be packed with different beads, which are derivatized with the one or more capture reagents, thereby capturing the sFlt-1 in a single place (see, antibody derivatized, bead-based technologies, e.g., the xMAP technology of Luminex (Austin, Tex.)).

After the test sample being assayed for sFlt-1 (or a fragment thereof) is brought into contact with at least one capture antibody (for example, the first capture antibody), the mixture is incubated in order to allow for the formation of a first antibody (or multiple antibody)-sFlt-1 (or a fragment thereof) complex. The incubation can be carried out at a pH of from about 4.5 to about 10.0, at a temperature of from about 2° C. to about 45° C., and for a period from at least about one (1) minute to about eighteen (18) hours, preferably from about 1 to about 24 minutes, most preferably for about 4 to about 18 minutes. The immunoassay described herein can be conducted in one step (meaning the test sample, at least one capture antibody and at least one detection antibody are all added sequentially or simultaneously to a reaction vessel) or in more than one step, such as two steps, three steps, etc.

After formation of the (first or multiple) capture antibody/sFlt-1 (or a fragment thereof) complex, the complex is then contacted with at least one detection antibody (under conditions which allow for the formation of a (first or multiple) capture antibody/sFlt-1 (or a fragment thereof)/second antibody detection complex). The at least one detection antibody can be the second, third, fourth, etc. antibodies used in the immunoassay. If the capture antibody/sFlt-1 (or a fragment thereof) complex is contacted with more than one detection antibody, then a (first or multiple) capture antibody/sFlt-1 (or a fragment thereof)/(multiple) detection antibody complex is formed. As with the capture antibody (e.g., the first capture antibody), when the at least second (and subsequent) detection antibody is brought into contact with the capture antibody/sFlt-1 (or a fragment thereof) complex, a period of incubation under conditions similar to those described above is required for the formation of the (first or multiple) capture antibody/sFlt-1 (or a fragment thereof)/(second or multiple) detection antibody complex. Preferably, at least one detection antibody contains a detectable label. The detectable label can be bound to the at least one detection antibody (e.g., the second detection antibody) prior to, simultaneously with, or after the formation of the (first or multiple) capture antibody/sFlt-1 (or a fragment thereof)/(second or multiple) detection antibody complex. Any detectable label known in the art can be used (see discussion above, including Polak and Van Noorden (1997) and Haugland (1996)).

The detectable label can be bound to the antibodies either directly or through a coupling agent. An example of a coupling agent that can be used is EDAC (1-ethyl-3-(3-dimethylaminopropyl) carbodiimide, hydrochloride), which is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as CPSP-Acridinium Ester (i.e., 9-[N-tosyl-N-(3-carboxypropyl)]-10-(3-sulfopropyl)acridinium carboxamide) or SPSP-Acridinium Ester (i.e., N10-(3-sulfopropyl)-N-(3-sulfopropyl)-acridinium-9-carboxamide).

The (first or multiple) capture antibody/sFlt-1/(second or multiple) detection antibody complex can be, but does not have to be, separated from the remainder of the test sample prior to quantification of the label. For example, if the at least one capture antibody (e.g., the first capture antibody) is bound to a solid support, such as a well or a bead, separation can be accomplished by removing the fluid (of the test sample) from contact with the solid support. Alternatively, if the at least first capture antibody is bound to a solid support, it can be simultaneously contacted with the sFlt-1-containing sample and the at least one second detection antibody to form a first (multiple) antibody/sFlt-1/second (multiple) antibody complex, followed by removal of the fluid (test sample) from contact with the solid support. If the at least one first capture antibody is not bound to a solid support, then the (first or multiple) capture antibody/sFlt-1/(second or multiple) detection antibody complex does not have to be removed from the test sample for quantification of the amount of the label.

After formation of the labeled capture antibody/sFlt-1/detection antibody complex (e.g., the first capture antibody/sFlt-1/second detection antibody complex), the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified by detecting the light emitted either visually or by using luminometers, x-ray film, high speed photographic film, a CCD camera, etc. Once the amount of the label in the complex has been quantified, the concentration of sFlt-1 or a fragment thereof in the test sample is determined by use of a standard curve that has been generated using serial dilutions of sFlt-1 or a fragment thereof of known concentration. Other than using serial dilutions of sFlt-1 or a fragment thereof, the standard curve can be generated gravimetrically, by mass spectroscopy and by other techniques known in the art.

In a chemiluminescent microparticle assay employing the ARCHITECT® analyzer, the conjugate diluent pH should be about 6.0+/−0.2, the microparticle coating buffer should be maintained at room temperature (i.e., at about 17 to about 27° C.), the microparticle coating buffer pH should be about 6.5+/−0.2, and the microparticle diluent pH should be about 7.8+/−0.2. Solids preferably are less than about 0.2%, such as less than about 0.15%, less than about 0.14%, less than about 0.13%, less than about 0.12%, or less than about 0.11%, such as about 0.10%.

FPIAs are based on competitive binding immunoassay principles. A fluorescently labeled compound, when excited by a linearly polarized light, will emit fluorescence having a degree of polarization inversely proportional to its rate of rotation. When a fluorescently labeled tracer-antibody complex is excited by a linearly polarized light, the emitted light remains highly polarized because the fluorophore is constrained from rotating between the time light is absorbed and the time light is emitted. When a "free" tracer compound (i.e., a compound that is not bound to an antibody) is excited by linearly polarized light, its rotation is much faster than the corresponding tracer-antibody conjugate produced in a competitive binding immunoassay. FPIAs are advantageous over RIAs inasmuch as there are no radioactive substances requiring special handling and disposal. In addition, FPIAs are homogeneous assays that can be easily and rapidly performed.

A commercially available anti-sFlt-1 antibody can be used in the methods of assay and kits there of. Commercially available anti-sFlt-1 antibodies include those available from Santa Cruz Biotechnology, Inc., and R&D Systems and those used in the Examples herein. Preferably, such commercially available antibodies are used as detection antibodies.

Any suitable control composition can be used in the sFlt-1 immunoassays. The control composition generally comprises sFlt-1 and any desirable additives.

Thus, in view of the above, a method of determining the presence, amount or concentration of sFlt-1 or a fragment thereof in a test sample is provided. The method comprises assaying the test sample for sFlt-1 (or a fragment thereof) by an immunoassay employing at least one antibody and at least one detectable label and comprising comparing a signal generated by the detectable label as a direct or indirect indication of the presence, amount or concentration of sFlt-1 in the test sample to a signal generated as a direct or indirect indication of the presence, amount or concentration of sFlt-1 in a calibrator. The calibrator is optionally part of a series of calibrators in which each of the calibrators differs from the other calibrators in the series by the concentration of sFlt-1. One of the at least one antibody is an isolated antibody, which specifically binds to sFlt-1 or a fragment thereof, and which has (i) a variable heavy domain region comprising the amino acid sequence of SEQ ID NO: 2, (ii) a variable light domain region comprising the amino acid sequence of SEQ ID NO: 4, or (iii) a variable heavy domain region comprising the amino acid sequence of SEQ ID NO: 2 and a variable light domain region comprising the amino acid sequence of SEQ ID NO: 4.

The method can comprise (i) contacting the test sample with at least one capture antibody, which binds to an epitope on sFlt-1 (or a fragment thereof), so as to form a capture antibody/sFlt-1 (or a fragment thereof) complex, (ii) contacting the capture antibody/sFlt-1 (or a fragment thereof) complex with at least one detection antibody, which comprises a detectable label and binds to an epitope on sFlt-1 (or a fragment thereof) that is not bound by the capture antibody, to form a capture antibody/sFlt-1 (or a fragment thereof)/detection antibody complex, and (iii) determining the amount of sFlt-1 (or a fragment thereof) in the test sample based on the signal generated by the detectable label in the capture antibody/sFlt-1 (or a fragment thereof)/detection antibody complex formed in (ii).

Alternatively, the method can comprise (i) contacting the test sample with at least one capture antibody, which binds to an epitope on sFlt-1 (or a fragment thereof) so as to form a capture antibody/sFlt-1 (or a fragment thereof) complex, and simultaneously or sequentially, in either order, contacting the test sample with detectably labeled sFlt-1 (or a fragment thereof), which can compete with any sFlt-1 (or a fragment thereof) in the test sample for binding to the at least one capture antibody. Any sFlt-1 (or a fragment thereof) present in the test sample and the detectably labeled sFlt-1 compete with each other to form a capture antibody/sFlt-1 (or a fragment thereof) complex and a capture antibody/detectably labeled sFlt-1 (or a fragment thereof) complex, respectively. The method further comprises (ii) determining the presence, amount or concentration of sFlt-1 in the test sample based on the signal generated by the detectable label in the capture antibody/detectably labeled sFlt-1 (or a fragment thereof) complex formed in (ii). The signal generated by the detectable label in the capture antibody/detectably labeled sFlt-1 (or a fragment thereof) complex is inversely proportional to the amount or concentration of sFlt-1 in the test sample.

The above methods can further comprise simultaneously or sequentially, in either order, determining the amount or concentration of VEGF (or a fragment thereof) and/or PlGF (or a fragment thereof) in the test sample. The method comprises assaying the test sample for VEGF (or a fragment thereof) and/or PlGF (or a fragment thereof) by an assay employing at least one specific binding partner for VEGF (or a fragment thereof) and/or at least one specific binding partner for PlGF (or a fragment thereof), respectively, and at least one detectable label and comprising comparing a signal generated by the detectable label as a direct or indirect indication of the amount or concentration of VEGF (or a fragment thereof) and/or PlGF (or a fragment thereof) in the test sample to a signal generated as a direct or indirect indication of the amount or concentration of VEGF (or a fragment thereof) and/or PlGF (or a fragment thereof), respectively, in a control or calibrator. The calibrator is optionally part of a series of calibrators in which each of the calibrators differs from the other calibrators in the series by the concentration of VEGF or PlGF, respectively.

The method can further comprise diagnosing, prognosticating, or assessing the efficacy of a therapeutic/prophylactic treatment of a patient from whom the test sample was obtained. If the method further comprises assessing the efficacy of a therapeutic/prophylactic treatment of the patient from whom the test sample was obtained, the method optionally further comprises modifying the therapeutic/prophylactic treatment of the patient as needed to improve efficacy. The method can be adapted for use in an automated system or a semi-automated system.

Generally, a predetermined level can be employed as a benchmark against which to assess results obtained upon assaying a test sample for sFlt-1 or a fragment thereof. Generally, in making such a comparison, the predetermined level is obtained by running a particular assay a sufficient number of times and under appropriate conditions such that a linkage or association of analyte presence, amount or concentration with a particular stage or endpoint of a disease, disorder or condition (e.g., preeclampsia or cardiovascular disease) or with particular indicia can be made. Typically, the predetermined level is obtained with assays of reference subjects (or populations of subjects). A level of sFlt-1 greater than 2 ng/mL, for example, can be indicative of preeclampsia or eclampsia. The sFlt-1 measured can include fragments thereof, degradation products thereof, and/or enzymatic cleavage products thereof.

In particular, with respect to a predetermined level as employed for monitoring disease progression and/or treatment, the amount or concentration of sFlt-1 or a fragment thereof may be "unchanged," "favorable" (or "favorably altered"), or "unfavorable" (or "unfavorably altered"). "Elevated" or "increased" refers to an amount or a concentration in a test sample that is higher than a typical or normal level or range (e.g., predetermined level), or is higher than another reference level or range (e.g., earlier or baseline sample). The term "lowered" or "reduced" refers to an amount or a concentration in a test sample that is lower than a typical or normal level or range (e.g., predetermined level), or is lower than another reference level or range (e.g., earlier or baseline sample). The term "altered" refers to an amount or a concentration in a sample that is altered (increased or decreased) over a typical or normal level or range (e.g., predetermined level), or over another reference level or range (e.g., earlier or baseline sample).

The typical or normal level or range for sFlt-1 is defined in accordance with standard practice. Because the levels of sFlt-1 in some instances will be very low, a so-called altered level or alteration can be considered to have occurred when there is any net change as compared to the typical or normal level or range, or reference level or range, that cannot be explained by experimental error or sample variation. Thus, the level measured in a particular sample will be compared with the level or range of levels determined in similar samples from a so-called normal subject. In this context, a "normal subject" is an individual with no detectable preeclampsia or cardiovascular disease, for example, and a "normal" (sometimes termed "control") patient or population is/are one(s) that exhibit(s) no detectable preeclampsia or cardiovascular disease, respectively, for example. Furthermore, given that sFlt-1 is not routinely found at a high level in the majority of the human population, a "normal subject" can be considered an individual with no substantial detectable increased or elevated amount or concentration of sFlt-1, and a "normal" (sometimes termed "control") patient or population is/are one(s) that exhibit(s) no substantial detectable increased or elevated amount or concentration of sFlt-1. An "apparently normal subject" is one in which sFlt-1 has not been or is being assessed. The level of an analyte is said to be "elevated" when the analyte is normally undetectable (e.g., the normal level is zero, or within a range of from about 25 to about 75 percentiles of normal populations), but is detected in a test sample, as well as when the analyte is present in the test sample at a higher than normal level. Thus, inter alia, the disclosure provides a method of screening for a subject having, or at risk of having, preeclampsia or a cardiovascular disease, or cancer, for example, as defined herein.

The method of assay can also involve the assay of other markers and the like. For example, the method of assay can also involve the assay of VEGF (decrease in level of) and/or PlGF (decrease in level of). Alternatively or additionally, the method of assay can involve the measurement of an obesity factor (e.g., body mass index (BMI); see, e.g., Sogin et al., U.S. Pat. App. Pub. No. 2008/0071151, which was published on Mar. 20, 2008, and is hereby incorporated by reference with regard to its teachings regarding same), and/or gestational age (GA).

Accordingly, the methods described herein also can be used to determine whether or not a subject has or is at risk of developing preeclampsia, or a cardiovascular disease, or cancer. Specifically, such a method can comprise the steps of:

(a) determining the concentration or amount in a test sample from a subject of sFlt-1 (or a fragment thereof) (e.g., using the methods described herein, or methods known in the art); and (b) comparing the concentration or amount of sFlt-1 (or a fragment thereof) determined in step (a) with a predetermined level, wherein, if the concentration or amount of sFlt-1 determined in step (a) is favorable with respect to a predetermined level, then the subject is determined not to have or be at risk for preeclampsia or a cardiovascular disease. However, if the concentration or amount of sFlt-1 determined in step (a) is unfavorable with respect to the predetermined level, then the subject is determined to have or be at risk for preeclampsia or a cardiovascular disease or cancer.

Additionally, provided herein is method of monitoring the progression of disease in a subject. Optimally the method comprising the steps of:

(a) determining the concentration or amount in a test sample from a subject of sFlt-1;

(b) determining the concentration or amount in a later test sample from the subject of sFlt-1; and (c) comparing the concentration or amount of sFlt-1 as determined in step (b) with the concentration or amount of sFlt-1 determined in step (a), wherein if the concentration or amount determined in step (b) is unchanged or is unfavorable when compared to the concentration or amount of sFlt-1 determined in step (a), then the disease in the subject is determined to have continued, progressed or worsened. By comparison, if the concentration or amount of sFlt-1 as determined in step (b) is favorable when compared to the concentration or amount of sFlt-1 as determined in step (a), then the disease in the subject is determined to have discontinued, regressed or improved.

Optionally, the method further comprises comparing the concentration or amount of sFlt-1 as determined in step (b), for example, with a predetermined level. Further, optionally the method comprises treating the subject with one or more pharmaceutical compositions for a period of time if the comparison shows that the concentration or amount of sFlt-1 as determined in step (b), for example, is unfavorably altered with respect to the predetermined level.

Still further, the methods can be used to monitor treatment in a subject receiving treatment with one or more pharmaceutical compositions. Specifically, such methods involve providing a first test sample from a subject before the subject has been administered one or more pharmaceutical compositions. Next, the concentration or amount in a first test sample from a subject of sFlt-1 is determined (e.g., using the methods described herein or as known in the art). After the concentration or amount of sFlt-1 is determined, optionally the concentration or amount of sFlt-1 is then compared with a predetermined level. If the concentration or amount of sFlt-1 as determined in the first test sample is lower than the predetermined level, then the subject is not treated with one or more pharmaceutical compositions. However, if the concentration or amount of sFlt-1 as determined in the first test sample is higher than the predetermined level, then the subject is treated with one or more pharmaceutical compositions for a period of time. The period of time that the subject is treated with the one or more pharmaceutical compositions can be determined by one skilled in the art (for example, the period of time can be from about seven (7) days to about two years, preferably from about fourteen (14) days to about one (1) year).

During the course of treatment with the one or more pharmaceutical compositions, second and subsequent test samples are then obtained from the subject. The number of test samples and the time in which said test samples are obtained from the subject are not critical. For example, a second test sample could be obtained seven (7) days after the subject is first administered the one or more pharmaceutical compositions, a third test sample could be obtained two (2) weeks after the subject is first administered the one or more pharmaceutical compositions, a fourth test sample could be obtained three (3) weeks after the subject is first administered the one or more pharmaceutical compositions, a fifth test sample could be obtained four (4) weeks after the subject is first administered the one or more pharmaceutical compositions, etc.

After each second or subsequent test sample is obtained from the subject, the concentration or amount of sFlt-1 is determined in the second or subsequent test sample is determined (e.g., using the methods described herein or as known in the art). The concentration or amount of sFlt-1 as determined in each of the second and subsequent test samples is then compared with the concentration or amount of sFlt-1 as determined in the first test sample (e.g., the test sample that was originally optionally compared to the predetermined level). If the concentration or amount of sFlt-1 as determined in step (c) is favorable when compared to the concentration or amount of sFlt-1 as determined in step (a), then the disease in the subject is determined to have discontinued, regressed or improved, and the subject should continue to be administered the one or pharmaceutical compositions of step (b). However, if the concentration or amount determined in step (c) is unchanged or is unfavorable when compared to the concentration or amount of sFlt-1 as determined in step (a), then the disease in the subject is determined to have continued, progressed or worsened, and the subject should be treated with a higher concentration of the one or more pharmaceutical compositions administered to the subject in step (b) or the subject should be treated with one or more pharmaceutical compositions that are different from the one or more pharmaceutical compositions administered to the subject in step (b). Specifically, the subject can be treated with one or more pharmaceutical compositions that are different from the one or more pharmaceutical compositions that the subject had previously received to decrease or lower said subject's sFlt-1 level.

Generally, for assays in which repeat testing may be done (e.g., monitoring disease progression and/or response to treatment), a second or subsequent test sample is obtained at a period in time after the first test sample has been obtained from the subject. Specifically, a second test sample from the subject can be obtained minutes, hours, days, weeks or years after the first test sample has been obtained from the subject. For example, the second test sample can be obtained from the subject at a time period of about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years after the first test sample from the subject is obtained. When used to monitor disease progression, the above assay can be used to monitor the progression of disease in subjects suffering from acute conditions. Acute conditions, also known as critical care conditions, refer to acute, life-threatening diseases or other critical medical conditions involving, for example, the cardiovascular system or excretory system. Typically, critical care conditions refer to those conditions requiring acute medical intervention in a hospital-based setting (including, but not limited to, the emergency room, intensive care unit, trauma center, or other emergent care setting) or administration by a paramedic or other field-based medical personnel. For critical care conditions, repeat monitoring is generally done within a shorter time frame, namely, minutes, hours or days (e.g., about 1 minute, about 5 minutes, about 10 minutes, about 15 minutes, about 30 minutes, about 45 minutes, about 60 minutes, about 2 hours, about 3 hours, about 4 hours, 4 about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days or about 7 days), and the initial assay likewise is generally done within a shorter timeframe, e.g., about minutes, hours or days of the onset of the disease or condition.

The assays also can be used to monitor the progression of disease in subjects suffering from chronic or non-acute conditions. Non-critical care or, non-acute conditions, refers to conditions other than acute, life-threatening disease or other critical medical conditions involving, for example, the cardiovascular system and/or excretory system. Typically, non-acute conditions include those of longer-term or chronic duration. For non-acute conditions, repeat monitoring generally is done with a longer timeframe, e.g., hours, days, weeks, months or years (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years), and the initial assay likewise generally is done within a longer time frame, e.g., about hours, days, months or years of the onset of the disease or condition.

Furthermore, the above assays can be performed using a first test sample obtained from a subject where the first test sample is obtained from one source, such as urine, serum or plasma. Optionally the above assays can then be repeated using a second test sample obtained from the subject where the second test sample is obtained from another source. For example, if the first test sample was obtained from urine, the second test sample can be obtained from serum or plasma. The results obtained from the assays using the first test sample and the second test sample can be compared. The comparison can be used to assess the status of a disease or condition in the subject.

Moreover, the present disclosure also relates to methods of determining whether a subject predisposed to or suffering from a disease (e.g., preeclampsia or a cardiovascular disease or cancer) will benefit from treatment. In particular, the disclosure relates to sFlt-1 companion diagnostic methods and products. Thus, the method of "monitoring the treatment of disease in a subject" as described herein further optimally also can encompass selecting or identifying candidates for therapy.

Thus, in particular embodiments, the disclosure also provides a method of determining whether a subject having, or at risk for, preeclampsia or a cardiovascular disease or cancer is a candidate for therapy. Generally, the subject is one who has experienced some symptom of preeclampsia or a cardiovascular disease or cancer or who has actually been diagnosed as having, or being at risk for, preeclampsia or a cardiovascular disease, or cancer and/or who demonstrates an unfavorable concentration or amount of sFlt-1 or a fragment thereof, as described herein.

The method optionally comprises an assay as described herein, where analyte is assessed before and following treatment of a subject with one or more pharmaceutical compositions (e.g., particularly with a pharmaceutical related to a mechanism of action involving sFlt-1), with immunosuppressive therapy, or by immunoabsorption therapy, with anti-angiogenic therapy, or where analyte is assessed following such treatment and the concentration or the amount of analyte is compared against a predetermined level. An unfavorable concentration of amount of analyte observed following treatment confirms that the subject will not benefit from receiving further or continued treatment, whereas a favorable concentration or amount of analyte observed following treatment confirms that the subject will benefit from receiving further or continued treatment. This confirmation assists with management of clinical studies, and provision of improved patient care.

For instance, the assays and kits optionally can be employed wherein the test sample is from a patient with signs and/or symptoms of an acute coronary syndrome and the method further comprises diagnosing or prognosticating the risk of experiencing a major adverse cardiac event (MACE). Assay of sFlt-1 as described herein optionally can be employed with other markers.

It goes without saying that, while certain embodiments herein are advantageous when employed to assess preeclampsia or a cardiovascular disease or cancer, the assays and kits also optionally can be employed to assess sFlt-1 in other diseases, disorders and conditions. For example, the integral role of growth factors in angiogenesis has been well documented. Additionally, sFlt-1 has been employed in antiangiogenic therapy in combination with immunotherapy with tumor-associated antigen (see, e.g., Cuadros et al., Cancer Research, 63:5895-5901 (2003)). For this and other reasons, assays as proposed herein can be employed, among other things, in assessment of cancer and cancer treatment.

The method of assay also can be used to identify a compound that ameliorates preeclampsia, cardiovascular disease, cancer and the like. For example, a cell that expresses sFlt-1 can be contacted with a candidate compound. The level of expression of sFlt-1 in the cell contacted with the compound can be compared to that in a control cell using the method of assay described herein.

The methods of assay as described herein further can be carried out where sFlt-1 is measured along with one or more other analytes, e.g., PlGF.

Adaptation of Kit and Method

The kit (or components thereof), as well as the method of determining the concentration of sFlt-1 in a test sample by an immunoassay as described herein, can be adapted for use in a variety of automated and semi-automated systems (including those wherein the solid phase comprises a microparticle), as described, e.g., in U.S. Pat. Nos. 5,089,424 and 5,006, 309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., analyte antibody or capture antibody) is attached (which can impact sandwich formation and analyte reactivity), and the length and timing of the capture, detection and/or any optional wash steps. Whereas a non-automated format such as an ELISA may require a relatively longer incubation time with sample and capture reagent (e.g., about 2 hours), an automated or semi-automated format (e.g., ARCHITECT®, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising the detection antibody labeled with alkaline phosphatase (or other label). Within the fluid pouch of the cartridge is an aqueous reagent that includes p-aminophenol phosphate.

In operation, a sample suspected of containing sFlt-1 is added to the holding chamber of the test cartridge and the cartridge is inserted into the I-STAT® reader. After the second antibody (detection antibody) has dissolved into the sample, a pump element within the cartridge forces the sample into a conduit containing the chip. Here it is oscillated to promote formation of the sandwich between the first capture antibody, sFlt-1, and the labeled second detection antibody. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of analyte IL-18 in the sample by means of an embedded algorithm and factory-determined calibration curve.

It further goes without saying that the methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an I-STAT® cartridge format, using a nucleic acid sequence linked to the signal antibody as a signal amplifier.

Furthermore, the methods and kits optionally are adapted for use on an automated or semi-automated system. Some of the differences between an automated or semi-automated system as compared to a non-automated system (e.g., ELISA) include the substrate to which the first specific binding partner (e.g., analyte antigen or capture antibody) is attached (which can impact sandwich formation and analyte reactivity), and the length and timing of the capture, detection and/or any optional wash steps. Whereas a non-automated format such as an ELISA may include a relatively longer incubation time with sample and capture reagent (e.g., about 2 hours) an automated or semi-automated format (e.g., ARCHITECT®) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT®) may have a relatively shorter incubation time (e.g., approximately 4 minutes for the ARCHITECT®).

Anti-sFlt-1 Antibody Pharmaceutical Composition

A pharmaceutical composition comprising a therapeutically or prophylactically effective amount of an isolated antibody that specifically binds to sFlt-1 or a fragment thereof is also provided. The antibody has a variable heavy domain region comprising the amino acid sequence of SEQ ID NO: 2, a variable light domain region comprising the amino acid sequence of SEQ ID NO: 4, or a variable heavy domain region comprising the amino acid sequence of SEQ ID NO: 2 and a variable light domain region comprising the amino acid sequence of SEQ ID NO: 4, and a pharmaceutically acceptable carrier, diluent, and/or excipient. Suitable carriers, diluents, and/or excipients are well-known in the art (see, e.g., *Remington's Pharmaceutical Sciences*, 20$^{th}$ edition, Gennaro, editor, Lippincott, Williams & Wilkins, Philadelphia, Pa., 2000). Optionally, the composition further comprises another active agent and/or an adjuvant. The pharmaceutical composition is optionally part of a kit comprising one or more containers in which the antibody, another active agent and/or the adjuvant can be present in the same or different containers.

Recombinant forms of antibodies, such as chimeric and humanized antibodies, can be used in pharmaceutical compositions to minimize the response by a human patient to the antibody. When antibodies produced in non-human subjects or derived from expression of non-human antibody genes are used therapeutically in humans, they are recognized to varying degrees as foreign, and an immune response may be generated in the patient. One approach to minimize or eliminate this immune reaction is to produce chimeric antibody derivatives, namely, antibody molecules that combine a non-human animal variable region and a human constant region. Such antibodies retain the epitope binding specificity of the original monoclonal antibody but may be less immunogenic when administered to humans and, therefore, more likely to be tolerated by the patient.

Chimeric monoclonal antibodies can be produced by recombinant DNA techniques known in the art. For example, a gene encoding the constant region of a non-human antibody molecule is substituted with a gene encoding a human constant region (see, for example, Int'l Pat. App. Pub. No. PCT/US86/02269, European Pat. App. 184,187, or European Pat. App. 171,496).

A chimeric antibody can be further "humanized" by replacing portions of the variable region not involved in antigen binding with equivalent portions from human variable regions. General reviews of "humanized" chimeric antibodies can be found in Morrison, Science 229: 1202-1207 (1985), and Oi et al., BioTechniques 4: 214 (1986). Such methods include isolating, manipulating, and expressing the nucleic acid sequences that encode all or part of an immunoglobulin variable region from at least one of a heavy or light chain. The cDNA encoding the humanized chimeric antibody, or a fragment thereof, can then be cloned into an appropriate expression vector. Suitable "humanized" antibodies can be alternatively produced by complementarity determining region (CDR) substitution (see, for example, U.S. Pat. No. 5,225,539; Jones et al., Nature 321: 552-525 (1986); Verhoeyan et al., Science 239: 1534 (1988); and Beidler et al., J. Immunol. 141: 4053-4060 (1988)).

Epitope imprinting also can be used to produce a "human" antibody polypeptide dimer that retains the binding specificity of the antibodies (e.g., hamster antibodies) specific for the human sFlt-1 or antigenically reactive fragment thereof. Briefly, a gene encoding a non-human variable region (VH) with specific binding to an antigen and a human constant region (CH1), is expressed in *E. coli* and infected with a phage library of human Vλ.Cλ genes. Phage displaying antibody fragments are then screened for binding to the human sFlt-1 protein. Selected human Vλ genes are recloned for expression of Vλ.Cλ. chains and *E. coli* harboring these chains are infected with a phage library of human VHCH1 genes and the library is subject to rounds of screening with antigen-coated tubes (see, e.g., Int'l Pat. App. Pub. No. WO 93/06213).

For administration to an animal, the pharmaceutical composition can be formulated for administration by a variety of routes. For example, the composition can be formulated for oral, topical, rectal or parenteral administration or for administration by inhalation or spray. The term "parenteral" as used herein includes subcutaneous, intravenous, intramuscular, intrathecal, and intrasternal injection and infusion techniques. Various diagnostic compositions and pharmaceutical compositions suitable for different routes of administration and methods of preparing pharmaceutical compositions are known in the art and are described, for example, in "*Remington: The Science and Practice of Pharmacy*" (formerly "*Remington's Pharmaceutical Sciences*"); Gennaro, A., Lippincott, Williams & Wilkins, Philadelphia, Pa. (2000). The pharmaceutical composition can be used in the treatment of various conditions in animals, including humans.

The pharmaceutical composition preferably comprises a therapeutically or prophylactically effective amount of an anti-sFlt-1 antibody. The term "therapeutically or prophylactically effective amount" as used herein refers to an amount of an anti-sFlt-1 antibody needed to treat, ameliorate, inhibit the onset, delay or slow the progression, or prevent a targeted disease, condition, or disorder or to exhibit a detectable therapeutic or preventative effect. For anti-sFlt-1 antibody, the therapeutically or prophylactically effective amount can be estimated initially, for example, either in cell culture assays or in animal models, usually in rodents, rabbits, dogs, pigs or primates. The animal model also can be used to determine the appropriate concentration range and route of administration. Such information then can be used to determine useful doses and routes for administration in the animal to be treated, including humans.

Examples of other active agents, which can be included in the pharmaceutical composition or administered simultaneously or sequentially, in either order, with the pharmaceutical composition, include, but are not limited to, an anti-hypertensive agent (e.g., adenosine, nifedipine, minoxidil, and magnesium sulfate), an angiogenic agent (e.g., VEGF, fibroblast growth factor (FGF), Sonic hedgehog (an indirect angiogenic agent), an SDF-1 mimetic (see, e.g., U.S. Pat. No. 7,368,425), an IGD peptide (see, e.g., U.S. Pat. No. 7,232,802) a hydrazide compound (see, e.g., U.S. Pat. App. Pub. No. 2008/0274158), a pro-angiogenesis, cytokine-stimulating peptide (see, e.g., U.S. Pat. App. Pub. No. 2008/0233081), an angiopoietin, such as angiopoietin-1, and the like. If the other active agent is administered simultaneously or sequentially, in either order, with the pharmaceutical composition, such as part of a separate pharmaceutical composition, desirably the other active agent is administered at such a time relative to the administration of the pharmaceutical composition comprising an anti-sFlt-1 antibody to realize at least an additive, preferably synergistic, effect.

The pharmaceutical composition comprising an anti-sFlt-1 antibody can be provided as a therapeutic kit or pack. Individual components of the kit can be packaged in separate containers, associated with which, when applicable, can be a notice in the form prescribed by a governmental agency regulating the manufacture, use or sale of pharmaceuticals or biological products, which notice reflects approval by the agency of manufacture, use or sale for human or animal administration. The kit can optionally further contain one or more other active agents for use in combination with the pharmaceutical composition comprising an anti-sFlt-1 antibody. The kit can optionally contain instructions or directions outlining the method of use or dosing regimen for the pharmaceutical composition comprising an anti-sFlt-1 antibody and/or additional active agents or adjuvants.

When one or more components of the kit are provided as solutions, for example an aqueous solution, or a sterile aqueous solution, the container means can itself be an inhalant, syringe, pipette, eye dropper, or other such like apparatus, from which the solution can be administered to a subject or applied to and mixed with the other components of the kit.

The components of the kit also can be provided in dried or lyophilized form, and the kit can additionally contain a suitable solvent for reconstitution of the lyophilized components. Irrespective of the number or types of containers, the kit also can comprise an instrument for assisting with the administration of the composition to a patient. Such an instrument can be an inhalant, a syringe, a pipette, a forceps, a measuring spoon, an eye dropper, or a similar, medically approved, delivery vehicle. Accordingly, the pharmaceutical composition optionally can be part of a kit comprising one or more containers in which the anti-sFlt-1 antibody, another active agent and/or the adjuvant can be present in the same or different containers.

Method of Prophylactic or Therapeutic Treatment

A method of treating a patient in therapeutic or prophylactic need of an antagonist of sFlt-1 is also provided. The method comprises administering to the patient a pharmaceutical composition comprising a therapeutically or prophylactically effective amount of an isolated antibody, which specifically binds to sFlt-1 or a fragment thereof, and which has (i') a variable heavy domain region comprising the amino acid sequence of SEQ ID NO: 2, (ii') a variable light domain region comprising the amino acid sequence of SEQ ID NO: 4, or (iii') a variable heavy domain region comprising the amino acid sequence of SEQ ID NO: 2 and a variable light domain region comprising the amino acid sequence of SEQ ID NO: 4. The composition further comprises a pharmaceutically acceptable carrier, diluent, and/or excipient. Optionally, the composition further comprises another active agent and/or an adjuvant. The method can prove useful in the treatment of preeclampsia, cardiovascular disease, and any disease, disorder or condition in which the inhibition of angiogenesis by sFlt-1 is undesirable, among others.

EXAMPLES

The following examples serve to illustrate the present disclosure. The examples are not intended to limit the scope of the claimed invention in any way.

Example 1

This example describes immunization of mice with human sFlt-1.

Female CAF1/J and RBF/DnJ mice (The Jackson Laboratory, Bar Harbor, Me.) were immunized six times with the sFlt-1 immunogen (sFlt-1 fused to C-terminal 6× histidine-tagged Fc region of human IgG and expressed in Sf21 cells using a baculovirus expression system, R&D Systems, Minneapolis, Minn.). The adjuvant alternated between the Freund's (Difco, Detroit, Mich.) and MPL+TDM (Corixa, Hamilton, Mont.) Adjuvant Systems, beginning with Freund's Complete Adjuvant, which was used for the primary inoculation. The inoculum was prepared by diluting the immunogen in 0.9% sodium chloride and emulsifying with one of the two adjuvants. At weeks 0, 3, 6, 8, 10 and 20 a 5 μg boost of the sFlt-1 immunogen was administered to the mice. Three days prior to the fusion, the mice were administered a final boost of 20 μg sFlt-1 domains 1-3 (Cell Sciences, Canton, Mass.). The immunogen was diluted in saline, and the inoculum was injected directly into the spleen and the body cavity surrounding the spleen for this final immunization.

Example 2

This example describes the screening of mice sera.

Sera samples, which were taken from the immunized mice 7-10 days following the final boost with immunogen, were tested in a 96-well microtiter chemiluminescence immunoassay (CIA) for reactivity to sFlt-1. Assay plates (NUNC Corporation, Rochester, N.Y.) were coated with 100 μL/well of rabbit anti-mouse IgG Fc antibody (Jackson Immuno Research, West Grove, Pa.) diluted to 5 μg/mL in phosphate-buffered saline (PBS). Plates were incubated overnight, and then the capture antibody was removed, followed by the addition of 200 μL/well fish gelatin diluted in PBS (block solution) for blocking. The plates were incubated and then washed with distilled water (dH$_2$O). Next, serial dilutions (in block solution) of the mouse sera or a positive control were added to the assay plates (100 μL/well), incubated and washed with dH$_2$O, Next, blocking solution (100 μL/well) or sFlt-1 (R&D Systems; diluted to 500 ng/mL in block solution) was added to the assay plates, after which the assay plates were incubated and subsequently washed. The tracer, PlGF-ACR (placental growth factor linked to acridinium and diluted to 10 ng/mL in block solution), was then added to the assay plates (100 μL/well), after which the assay plates were incubated and subsequently washed. Finally, using a Microbeta Jet instrument (PerkinElmer, Waltham, Mass.), pre-trigger and trigger reagents (both Abbott Laboratories, Abbott Park, Ill.) were added, and the chemiluminescent signal was read. Samples were ranked based upon strength of signal.

Example 3

This example describes the production of hybridomas.

Mice were euthanized, and their spleens were harvested and placed into Hybridoma Serum-Free Medium (HSFM) (Invitrogen) supplemented only with L-glutamine (Invitrogen). A cell fusion was performed as described by Kohler and Milstein (Nature 256: 495-497 (1975)). Each mouse spleen was placed into a separate petri dish containing HSFM with L-glutamine. The splenocytes were perfused out of each spleen using a syringe containing HSFM with L-glutamine and a cell scraper, and then counted using a hemocytometer. Splenocytes (6E6) from each mouse were pooled and mixed with an equal number (1.8E7) of SP 2/0 myeloma cells and centrifuged into a pellet. The fusion was accomplished by exposing the splenocytes and SP 2/0 cells to 50% polyethylene glycol (PEG) (molecular weight 1300-1600, ATCC, Manassas, Va.) in HSFM. One mL of the PEG solution was added to the cell pellet over 30 seconds, followed by an additional one-minute incubation. The PEG and cell pellet were diluted by slowly adding 30 mL of HSFM with L-glutamine over 30 seconds. The fused cells were then removed from suspension by centrifuging and subsequently decanting the supernatant. The cell pellet was re-suspended into a 50/50 volume/volume mixture of HSFM with L-glutamine and spent media (i.e., the media in which the myelomas were cultured in and which contains cell-secreted growth factors). This media mixture was supplemented with 15% fetal bovine serum (FBS; Hyclone Laboratories, Logan, Utah), HAT (Hypoxanthine, Aminopterin, Thymidine) (Sigma Laboratories, St. Louis, Mo.), HT supplement (Invitrogen), Hybridoma Cloning Factor (Bioveris Corporation, Gaithersburg, Md.), and additional L-glutamine in order to select for hybridomas. The cells were plated at 0.2 mL per well into 96-well cell culture plates. At days 5 and 7 about one half of the medium in each well was removed by aspiration and replaced with HSFM supplemented with 15% FBS, HT supplement, and L-glutamine. Hybridomas were allowed to grow for 10 or 13 days, from the day of fusion, prior to supernatant screening for antibody production.

Example 4

This example describes the screening and selection of hybridomas.

Samples of supernatants from hybridomas were analyzed for anti-sFlt-1 antibodies using a CIA. Assay plates (NUNC) were coated with 100 μL/well of rabbit anti-mouse IgG Fc antibody diluted to 5 μg/mL in PBS. Plates were incubated overnight, the capture antibody was removed, and fish gelatin (diluted in PBS (block solution)) was added (200 μL/well) for blocking. The plates were incubated and then washed with $dH_2O$. Cell supernatants (100 μL/well) were added to the blocked plates and allowed to incubate at room temperature for at least one hour. Next, sFlt-1 antigen (250 ng/mL in blocking solution, 100 μL/well) was added to the assay plates, and the plates were incubated and subsequently washed with $dH_2O$. Next, PlGF-ACR (10 ng/mL in block solution, 100 μL/well) was added to the assay plates, and the plates were incubated and subsequently washed. Finally, using a Microbeta Jet instrument, pre-trigger and trigger reagents were added, and the chemiluminescent signal was read. Positives were selected based upon strength of signal. Positive hybrids were expanded to 24-well plates in HSFM supplemented with 1% L-glutamine, 10% FBS, and HT supplement. Following 3-7 days growth, the 24-well cultures were again evaluated by CIA as described in this example, except multiple dilutions of antibody were tested for reactivity to both sFlt-1 and blocking solution (blocking solution used as a control). Hybrids that demonstrated a relatively high reactivity to sFlt-1 in this assay were expanded to culture flasks. Hybrid 1-833 was cloned using a FACS (fluorescence-activated cell sorter) Aria instrument (Becton Dickinson, Franklin Lakes, N.J.). Parameters on the FACS were set so that the instrument identified single cells and sorted them into 96-well plates at 1 cell/well. The cells were cultured for 7-10 days in HSFM containing L-glutamine, FBS and HT, as previously described. Cell supernatant was again tested by CIA for reactivity to sFlt-1 using the method previously described. Clone 1-833-217 was identified as sFlt-1-reactive, and cells were transferred to a 24-well cell culture plate. Cells were then cultured in HSFM containing L-glutamine, FBS and HT for 3-5 days, after which the supernatant was tested (as described) and found to contain antibodies specifically reactive to sFlt-1. The 1-833-217 cell line was weaned to growth in serum-free media (HSFM supplemented only with L-glutamine) after which it was subcloned at 1 cell/well via the FACS Aria (as described) into wells containing HSFM supplemented with L-glutamine. Screening at the 96-well stage (as described) identified subclone 1-833-527 as sFlt-1-reactive. Secondary screening at the 24-well stage (as described) confirmed that this clone was specifically reactive to sFlt-1. A cell bank for 1-833-527 clone is stored in liquid nitrogen.

Example 5

This example describes competitive inhibition testing.

Testing was done to determine whether or not the 1-833-217 antibody binds to the same epitope on sFlt-1 as previously existing, commercially available antibodies. Assay plates (NUNC) were coated with 100 μL/well of PlGF (R&D Systems) diluted to 500 ng/mL in PBS and incubated overnight. The PlGF was removed, and plates were blocked with 200 μL/well blocking solution (bovine serum albumin (BSA) diluted in PBS). The plates were then incubated for about 30 minutes and washed with $dH_2O$. Next, sFlt-1 (diluted to 500 ng/mL in PBS) was added to each assay well (100 μL/well), and the plates were incubated for 2-3 hours and then subsequently washed with $dH_2O$. Next, unlabeled antibodies (diluted to 10 μg/mL in PBS) were added to the appropriate assay wells (100 μL/well) and incubated for 2-3 hours. Next, 50 μL of biotin-labeled 1-833-217 antibody, diluted to 250 ng/mL in blocking solution, were added to each assay well (note that the unlabeled antibody was not removed prior to adding the biotin-labeled antibody). The plates were incubated for 10 minutes, the reagents were removed, and the plates were washed with $dH_2O$. Next, 100 μL of peroxidase-conjugated streptavidin (Jackson ImmunoResearch), diluted to 200 ng/mL in blocking solution, were added to each assay well. The plates were incubated for about 30 minutes and then washed with $dH_2O$. O-phenylenediamine substrate (OPD) was used as the chromogen to generate signal. The reaction was quenched using 1 N sulfuric acid. Signal was read at a wavelength of 492 nm. Results from the assay indicated that the 1-833-217 clone binds to a different epitope on sFlt-1 vs. either of the two commercially available antibodies, i.e., clone 43 (R&D Systems) and clone 321 (catalog no. MAB321, hereafter "monoclonal antibody 321," R&D Systems).

Example 6

This example describes the characterization of the affinities/kinetics of anti-sFlt-1 monoclonal antibodies for sFlt-1 antigen (domains 1-3). The affinities/kinetics of anti-human sFlt-1 monoclonal antibodies 1-654-302, 1-833-217, and 1-833-527 for sFlt-1 antigen (domains 1-3; R&D Systems) were determined using a BIAcore 2000 instrument (BIAcore, GE Healthcare, Piscataway, N.J.). First, a ~5,000 RU rabbit anti-mouse IgG Capture Biosensor was created by amine-coupling rabbit anti-mouse IgG antibody (BIAcore, GE Healthcare) to a CM4 biosensor chip (BIAcore, GE Healthcare) via EDC/NHS/ethanolamine chemistry provided in an Amine Coupling Kit (BIAcore, GE Healthcare). sFlt-1 antibody and sFlt-1 antigen (domains 1-3) were diluted into a running buffer (hereinafter "running buffer") composed of HBS-EP buffer (BIAcore, GE Healthcare) spiked with 1% BSA, 1% CM-Dextran, and 0.1% Tween 20. Each sFlt-1 antibody was diluted to 1 μg/mL, and sFlt-1 antigen (domains 1 through 3) was diluted to concentrations ranging from 2.56 to 250 nM using a 2.5-fold dilution series. After equilibrating the rabbit anti-mouse IgG Capture Biosensor for 5 minutes at 10 μL/minute with running buffer, sFlt-1 antibody (9-14 μL) was injected over individual flow cells with one flow cell being left blank as a reference flow cell. The flow cells were washed for 5 minutes at 60 μL/minute with running buffer. Then 150 μL of sFlt-1 antigen at a random concentration were injected across the biosensor. The biosensor was subsequently washed for 6 minutes at 60 μl/minute with running buffer. The biosensor was regenerated with one 30 μL injection of 10 mM glycine, pH 1.7 (BIAcore, GE Healthcare), at a flow rate of 10 μL/minute. All concentrations of sFlt-1 antigen were tested in duplicate. The binding kinetics (association and dissociation) were monitored via sensorgrams. The sensorgrams were double-referenced and fit to a 1:1 binding model using Scrubber 2.0 software (BioLogic Software Pty Ltd., Australia) to determine association and dissociation rates, as well as overall $K_D$. The results are shown in Table 1.

TABLE 1

| sFlt-1 monoclonal antibody | $k_{on}$ (M$^{-1}$s$^{-1}$) | $k_{off}$ (s$^{-1}$) | $K_D$ (M) |
|---|---|---|---|
| 1-654-302 | 1.712(4) × 10$^6$ | 4.9(1) × 10$^{-4}$ | 2.87(6) × 10$^{-10}$ |
| 1-833-217 | 1.936(5) × 10$^6$ | 4.1(1) × 10$^{-4}$ | 2.14(7) × 10$^{-10}$ |
| 1-833-527 | 1.895(6) × 10$^6$ | 4.0(2) × 10$^{-4}$ | 2.13(9) × 10$^{-10}$ |

Standard errors of determined values are reported in parentheses with respect to the smallest number place value.

Example 7

This example describes the screening of various anti-sFlt-1 monoclonal antibodies in a double monoclonal antibody sandwich assay.

Nineteen monoclonal antibodies obtained in accordance with the methods set forth herein and 4 monoclonal antibodies obtained from R&D Systems were screened using a chemiluminescent microparticle immunoassay employing the ARCHITECT® automated analyzer (Abbott Laboratories; see, also, U.S. Pat. Nos. 5,795,784 and 5,856,194, both of which are incorporated herein by reference in their entireties). An sFlt-1 antigen (sFlt-1 domains 1-3 from mouse myeloma NS0, sFlt-1 domains 1-3:Fc chimera from mouse myeloma NS0, or sFlt-1 domains 1-6:Fc chimera from Sf21 cells using baculovirus) was contacted with a microparticle reagent, which contained paramagnetic, streptavidin-coated microparticles coated (300 ng/mL) with biotin-labeled anti-sFlt-1 monoclonal antibody or paramagnetic microparticles coated with anti-sFlt-1 monoclonal antibody chemically attached to the microparticles with EDAC (1-ethyl-3-(3-dimethylaminopropyl)carbodiimide, hydrochloride), and allowed to react for 18 minutes at 37° C. on the ARCHITECT® analyzer. After the 18-minute reaction, the microparticles were washed to eliminate any unbound sFlt-1 antigen, CPSP-conjugated or SPSP-conjugated anti-sFlt-1 monoclonal antibody (300 ng/mL) was added, and the sample was incubated for four minutes on the ARCHITECT® analyzer. The CPSP/SPSP-conjugated anti-sFlt-1 monoclonal antibody bound to the sFlt-1 antigen already bound to the anti-sFlt-1 monoclonal antibody coated on the microparticles. After four minutes, the unbound conjugate was eliminated by washing, and pre-trigger and trigger solutions were added to cause a chemiluminescent reaction, which was measured in relative light units (RLUs). A sandwich was considered to be positive if the RLU for the calibrator at 1,000 pg/mL was greater than 400,000.

The results are set forth in FIG. 3. Anti-sFlt-1 monoclonal antibody 1-780-103 and 2-106-105 coated on microparticles formed sandwiches with a number of other antibodies. Anti-sFlt-1 monoclonal antibody 1-780-103 and R&D Systems' monoclonal antibody 321, 49508 and 49566 may have fast "on" rates and can form sandwiches with multiple antibodies. Anti-sFlt-1 monoclonal antibody 1-330-202 and 1-333-205 and R&D Systems' 49508 react with sFlt-1 domains 1-6:Fc chimera only and may bind to a region outside of domains 1-3. Anti-sFlt-1 monoclonal antibody 2-106-105 may have a slow "on" rate and cannot be used as the conjugate. Anti-sFlt-1 monoclonal antibodies, which cannot form sandwiches with PlGF-acridinium may be used to detect free sFlt-1 (like 49566). Anti-sFlt-1 monoclonal antibody 1-330-202, 1-333-205, and 2-154-307 and R&D Systems' 49511 have no or limited reactivity.

Example 8

This example describes the use of various combinations of anti-sFlt-1 monoclonal antibodies in the detection of total sFlt-1 and free sFlt-1.

A composition comprising a fixed amount of sFlt-1 was prepared. Varying amounts of PlGF (0-100 molar excess), which complexes with sFlt-1, were added to separate aliquots of the sFlt-1 composition. Various combinations of monoclonal antibodies were assayed for their ability to detect free sFlt-1 (i.e., sFlt-1 that is not complexed with PlGF) and total sFlt-1 (i.e., sFlt-1 that is complexed with PlGF and free sFlt-1). A chemiluminescent microparticle immunoassay employing the ARCHITECT® automated analyzer as described in Example 7 was used. In one format, the microparticles (0.10% solid) were coated with monoclonal antibody 1-833-527, and the R&D Systems monoclonal antibody 321 was used as the conjugate (the 527/321 format). In another format, the microparticles (0.05% solid) were coated with the R&D Systems monoclonal antibody 49566, and the R&D Systems monoclonal antibody 321 was used as the conjugate (the 566/321 format). In yet another format, the microparticles (0.10% solid) were coated with the R&D Systems monoclonal antibody 321, and PlGF was used as the conjugate (the 321/PlGF format). The results, expressed in RLUs and relative RLUs, are set forth in Table 2.

TABLE 2

| [PlGF] | Format | | | | | |
|---|---|---|---|---|---|---|
| | RLUs | | | Relative RLUs | | |
| nM | 527/321 | 566/321 | 321/PlGF | 527/321 | 566/321 | 321/PlGF |
| 0.0 | 1104966 | 745206 | 1126081 | 1.00 | 1.00 | 1.00 |
| 0.2 | 1093205 | 742865 | 1048390 | 0.99 | 1.00 | 0.93 |
| 0.4 | 1090443 | 743200 | 976763 | 0.99 | 1.00 | 0.87 |
| 0.8 | 1045042 | 718955 | 838054 | 0.95 | 0.96 | 0.74 |
| 1.6 | 1036661 | 646194 | 621663 | 0.94 | 0.87 | 0.55 |
| 3.2 | 1012088 | 506651 | 382994 | 0.92 | 0.68 | 0.34 |
| 6.4 | 1032870 | 420755 | 274102 | 0.93 | 0.56 | 0.24 |
| 12.9 | 1014395 | 359070 | 226242 | 0.92 | 0.48 | 0.20 |
| 25.8 | 1030129 | 302275 | 191487 | 0.93 | 0.41 | 0.17 |
| 51.5 | 1032753 | 248866 | 172991 | 0.93 | 0.33 | 0.15 |
| 103.0 | 1028819 | 205840 | 166618 | 0.93 | 0.28 | 0.15 |
| 206.0 | 1029538 | 183671 | 157486 | 0.93 | 0.25 | 0.14 |

Thus, these findings confirm that the 527/321 format enabled an assay for total sFlt-1.

Example 9

This example describes the sequencing of the anti-sFlt-1 monoclonal antibody 1-833-527.

mRNA was extracted from hybridoma cell cultures using commercially available reagents (Oligotex direct mRNA kit, Qiagen, Inc., Valencia, Calif.) following the manufacturer's recommendations. IgG heavy chain cDNA and kappa light chain cDNA were generated from the extracted mRNA using commercially available murine Ig primers, MuIgGVH3'-2 and MuIgkVL3'-1, respectively (Mouse Ig-Primer set, Novagen, EMD Chemicals, Inc., Gibbstown, N.J.), following standard protocols. The variable heavy (VH) and variable light (VL) genes were then amplified from their respective cDNA using polymerase chain reaction (PCR) and pools of IgG- and IgK-specific primers from the same commercially available murine Ig primer kits referenced above using standard protocols. Amplified VH and VL PCR products were cloned into a commercially available vector (pCR2.1-TOPO cloning kit, Qiagen, Inc.) per the manufacturer's directions and transformed into E. coli. Sequence analysis was performed (BigDye Terminator v3.1 cycle sequencing kit, Applied Biosystems, Foster City, Calif.) on plasmids isolated from multiple transformed E. coli colonies to identify the VH and VL gene sequences. The sequences are set forth in FIGS. 1-2. FIG. 1 shows the nucleotide (SEQ ID NO: 1) and amino acid (SEQ ID NO: 2) sequences of the variable heavy chain (VH) regions of the anti-sFlt-1 monoclonal antibody 1-833-527. FIG. 2 sets forth the nucleotide (SEQ ID NO: 3) and amino acid (SEQ ID NO: 4) sequences of the variable light chain (VL) regions of the anti-sFlt-1 monoclonal antibody 1-833-527.

Furthermore, sequencing data confirmed that the anti-sFlt-1 monoclonal antibody 1-833-527 had the identical nucleotide sequence as the anti-sFlt-1 monoclonal antibody 1-833-217 described in Example 4.

Example 10

This example describes the reference range of sFlt-1 in an apparently healthy population.

An immunoassay employing the anti-sFlt-1 monoclonal antibody 1-833-527 immobilized on paramagnetic microparticles as the capture reagent and acridinium labeled R&D Systems anti-sFlt-1 monoclonal antibody 321 as the detection reagent was used to test specimens on the ARCHITECT® analyzer as described in Example 7. R&D Systems sFlt-1 antigen domains 1-3:Fc chimera was used as calibrator material. A calibrator set consisting of concentrations of 0, 125, 400, 2,500, 12,000 and 50,000 pg/mL was used to calibrate the assay. The functional sensitivity of the assay in this configuration provided a 10% CV at a concentration less than 90 pg/mL and a 20% CV at a concentration less than 20 pg/mL. (The % Coefficient of Variation is (CV) is defined as the standard deviation of a measurement (SD) divided by the mean analyte concentration and multiplied by 100.)

Following institutional review board approval and informed consent from the subjects, serum and EDTA plasma was obtained from 305 apparently healthy volunteers between ages 18 and 81 years with no history of cardiac disease, diabetes, or hypertension. The plasma specimens were placed on ice after collection and processed within 4 to 6 hours. The serum specimens were allowed to clot at ambient temperature for 30 minutes, then placed on ice and processed within 4 to 6 hours. After processing, the serum and plasma were aliquoted and frozen at less than −60 degrees C. or colder. Prior to testing on the ARCHITECT® analyzer, the specimens were thawed and centrifuged at greater than 2,000×g for at least 10 minutes.

Descriptive statistics for sFlt-1 (pg/mL) concentrations in this population are described in Tables 3 and 4 below. The median concentrations in the two specimen types are equivalent across gender and age groups. The median of the serum specimens is approximately 50 pg/mL or 20% higher than the median observed in EDTA plasma.

TABLE 3

| EDTA Plasma | | | | | |
|---|---|---|---|---|---|
|  | All | Male | Female | Age ≧40 | Age <40 |
| Number (N) | 303 | 126 | 177 | 169 | 134 |
| Mean | 252.9 | 256.6 | 250.3 | 258.3 | 246.1 |
| Standard Deviation | 38.2 | 34.3 | 40.6 | 40.2 | 34.3 |
| Minimum | 160.6 | 179.4 | 160.6 | 160.6 | 172.0 |
| Maximum | 412.6 | 351.4 | 412.6 | 412.6 | 344.9 |
| Quantiles | | | | | |
| 5% | 195.1 | 202.8 | 187.3 | 199.5 | 189.5 |
| 10% | 205.7 | 215.1 | 199.3 | 208.4 | 199.3 |
| 25% | 227.4 | 234.4 | 225.6 | 235.0 | 224.2 |
| 50% (Median) | 248.8 | 251.4 | 246.0 | 250.8 | 244.6 |
| 75% | 275.8 | 280.2 | 274.0 | 281.3 | 269.3 |
| 90% | 304.2 | 307.2 | 298.4 | 317.9 | 290.2 |
| 95% | 322.9 | 322.5 | 325.8 | 332.9 | 306.3 |

TABLE 4

| Serum | | | | | |
|---|---|---|---|---|---|
|  | All | Male | Female | Age ≧40 | Age <40 |
| Number (N) | 305 | 127 | 178 | 168 | 137 |
| Mean | 304.0 | 305.9 | 302.7 | 308.7 | 298.3 |
| Standard Deviation | 42.3 | 38.2 | 45.0 | 43.9 | 39.5 |
| Minimum | 212.3 | 231.4 | 212.3 | 212.3 | 225.6 |
| Maximum | 444.9 | 444.9 | 439.6 | 444.9 | 412.3 |
| Quantiles | | | | | |
| 5% | 239.7 | 247.8 | 238.8 | 245.5 | 236.7 |
| 10% | 252.5 | 257.1 | 250.3 | 257.6 | 249.0 |
| 25% | 272.9 | 276.9 | 269.2 | 278.6 | 268.3 |
| 50% (Median) | 299.9 | 303.3 | 299.3 | 301.9 | 298.1 |
| 75% | 331.3 | 331.1 | 331.6 | 331.0 | 331.5 |
| 90% | 358.2 | 354.8 | 360.2 | 364.0 | 352.4 |
| 95% | 380.2 | 367.1 | 391.3 | 400.1 | 360.7 |

Example 11

This example describes the use of an exemplary sFlt-1 assay as described herein in a patient population at risk for cardiovascular events.

Specimens from a prospective, blinded, multi-center cohort clinical study were evaluated using the ARCHITECT® sFlt-1 assay described in Example 10. Patients in the study were recruited at presentation to the emergency department with chest pain and signs/symptoms of ischemia suggestive of acute coronary syndrome (ACS). Institutional review boards at each site approved the study protocol, and informed consent was obtained from all subjects. Data regarding clinical characteristics, cardiac procedures and cardiac events during hospitalization were collected. Telephone follow up occurred at 30 days and approximately one year after enrollment to assess for major adverse cardiac events (MACE) which consisted of death, myocardial infarction, or revascularization.

Patient blood samples were obtained in lithium heparin plasma, EDTA plasma, and serum collection tubes at enrollment (0 hours), 4 to 8 hours later, and if still hospitalized, 12 to 16 hours after enrollment. Blood was collected and processed according to local site procedures. Samples were stored centrally at less than −60 degrees C. prior to analysis. Prior to testing on the ARCHITECT® analyzer, the specimens were thawed and centrifuged at greater than 2,000×g for at least 10 minutes.

Serum specimens from a total of 497 patients were available for evaluation in the sFlt-1 assay. Lithium heparin plasma specimens were used for evaluation in the commercially available ARCHITECT® Troponin I assay. There were 80 patients (16.1%) in this group that experienced MACE between presentation to the emergency department and the one year follow up. The descriptive characteristics of sFlt-1 are shown below in Table 5. A significant increase in sFlt-1 was observed in the patients that experienced MACE compared to those that did not have a cardiac event. The Wilcoxon test was used to determine statistical significance (p-value <0.0001) between the median concentrations of the patients with and without MACE.

TABLE 5

Descriptive characteristics of sFlt-1 (pg/mL) in the clinical study.

|  | Total Patients (N = 497) | Patients without MACE (N = 417) | Patients with MACE (N = 80) |
|---|---|---|---|
| Mean | 936.3 | 770.9 | 1798.4 |
| Standard Deviation | 3050.5 | 3011.8 | 3124.6 |
| Minimum | 149.8 | 149.8 | 215.5 |
| Maximum | 40646.6 | 40646.6 | 17863.5 |
| Quantiles |  |  |  |
| 25% | 267.9 | 264.1 | 317.5 |
| 50% (median) | 310.9 | 301.9 | 418.1 |
| 75% | 392.6 | 359.9 | 1391.8 |

Further analysis of the clinical data was made by stratifying patients using the upper limit of the sFlt-1 reference interval in serum specimens (95th percentile, 380 pg/mL) and the ARCHITECT® Troponin I at the 99th percentile (0.028 ng/mL) as stated in the package insert. There are 424 patients with Troponin I values less than the 99th percentile and 38 (9.0%) of these patients experienced MACE. Of the 424 Troponin I negative patients; there are 87 patients with sFlt-1 concentration greater than the 95th percentile with a 19.5% incidence of MACE compared to a 6.2% incidence of MACE in the 337 patients that are sFlt-1 negative (see FIG. 4). The difference in event rates observed when the Troponin I negative group is stratified by sFlt-1 is statistically significant (p-value equal to 0.0003) using the Fisher's Exact test.

Example 12

This example describes the use of an exemplary sFlt-1 assay as described herein to assess sFlt-1 in a population of pregnant women.

Specimens from a prospective, blinded, multi-center cohort clinical study were evaluated using the ARCHITECT® sFlt-1 assay described in Example 10. Institutional review boards at each site approved the study protocol and informed consent was obtained from all subjects. Subjects were enrolled in the study at estimated gestational age less than or equal to 15 weeks. Serum and EDTA plasma were collected at enrollment, additional specimens were collected at approximately 16-20 weeks, 24-28 weeks, and 34-38 weeks gestational age if still pregnant. At each visit blood pressure, urinary protein, and weight was recorded as part of standard clinical care. For hypertensive patients, the specific hypertensive condition suggested by the patient's medical conditions was categorized based on the American College of Obstetricians and Gynecologists recommendations pertaining to preeclampsia. An additional specimen was collected as an option in subjects diagnosed with preeclampsia between the time of diagnosis and delivery. Blood was collected and processed according to local site procedures. Samples were stored centrally at less than −60 degrees C. prior to analysis. Prior to testing on the ARCHITECT® analyzer, the specimens were thawed and centrifuged at greater than 2,000×g for at least 10 minutes.

To measure pregnancy samples, a calibrator providing as assay range from 0 to 150 ng/mL was employed consisting of concentrations of 0, 2.5, 10, 35, 75 and 150 ng/mL to calibrate the assay. EDTA plasma specimens (n=2,458) from a total of 653 patients were available for evaluation in the ARCHITECT® sFlt-1 assay. The sFlt-1 values were plotted against the gestational age for each specimen as shown in FIG. 5, a rise in sFlt-1 concentration of approximately 20% is observed with increasing gestational age.

Figure 6:
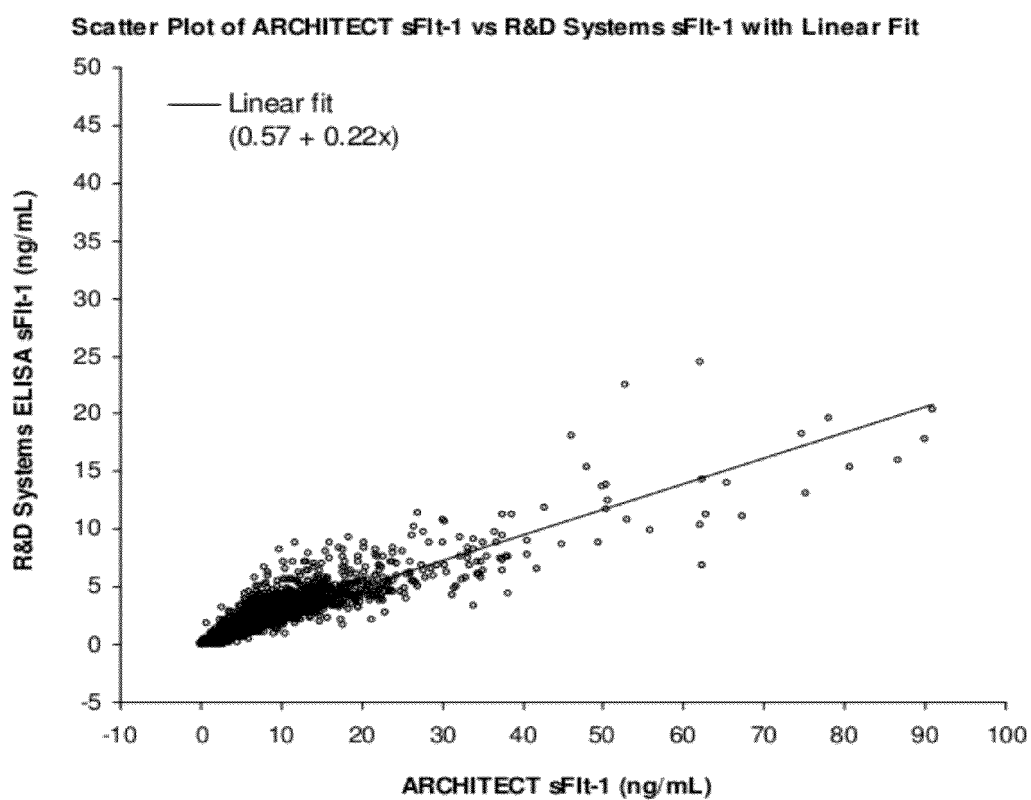
FIG. 6 is a scatter plot with linear fit of the ARCHITECT® sFlt-1 assay as described in Example 12 vs. R&D Systems sFlt-1 assay.

The specimens (n=2,453) were also evaluated in the commercially available R&D Systems Human sVEGF R1 (sFlt-1) ELISA assay (Catalog #DVR100). The correlation is shown in FIG. 6, linear regression results in the fit: R&D Systems sFlt-1=0.223*(ARCHITECT sFlt-1)+0.571 with a Spearman correlation coefficient, r=0.897. The sample concentrations ranged from 0.1 to 91.0 ng/mL on the ARCHITECT sFlt-1 assay.

Figure 5:
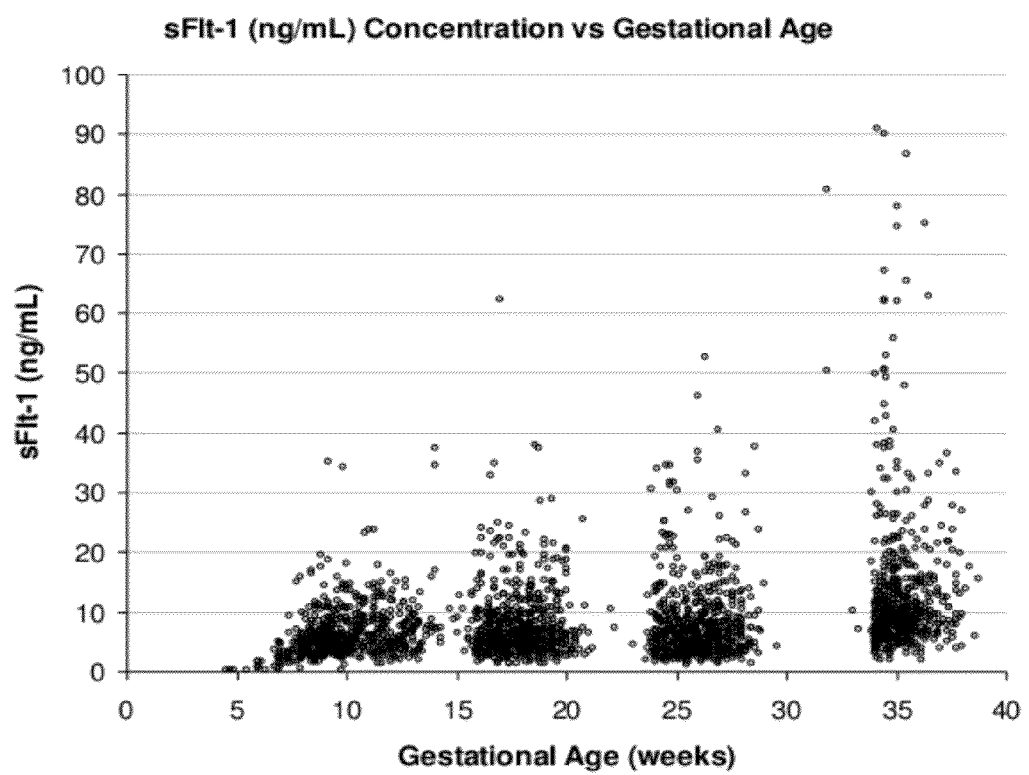
FIG. 5 is a scatter plot of sFlt-1 (ng/mL) Concentration vs. Gestational Age (weeks), as described in Example 12.

All of the data points in FIGS. 5 and 6 are represented as open circles; regions that appear to be solid are due to overlap in data points in the large sample sets.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

What is claimed is:

1. An isolated antibody that specifically binds to soluble FMS-like tyrosine kinase-1 (sFlt-1) or a fragment of the antibody that specifically binds to sFlt-1, wherein the antibody has (i) a variable heavy domain region comprising the amino acid sequence of SEQ ID NO: 2, (ii) a variable light domain region comprising the amino acid sequence of SEQ ID NO: 4, or (iii) a variable heavy domain region comprising the amino acid sequence of SEQ ID NO: 2 and a variable light domain region comprising the amino acid sequence of SEQ ID NO: 4.

2. A kit for assaying a test sample for sFlt-1 (or a fragment thereof), which kit comprises at least one component for assaying the test sample for sFlt-1 (or a fragment thereof) and instructions for assaying the test sample for sFlt-1 (or a fragment thereof), wherein the at least one component includes at least one composition comprising an isolated antibody that specifically binds to sFlt-1 or a fragment of the antibody that specifically binds to sFlt-1, wherein the antibody has (i) a variable heavy domain region comprising the amino acid sequence of SEQ ID NO: 2, (ii) a variable light domain region comprising the amino acid sequence of SEQ ID NO: 4, or (iii) a variable heavy domain region comprising the amino acid sequence of SEQ ID NO: 2 and a variable light domain region comprising the amino acid sequence of SEQ ID NO: 4, wherein the antibody is optionally detectably labeled.

3. A pharmaceutical composition comprising (i) a therapeutically or prophylactically effective amount of an isolated antibody, which specifically binds to sFlt-1, or a fragment of the antibody that specifically binds to sFlt-1, wherein the antibody has (i') a variable heavy domain region comprising the amino acid sequence of SEQ ID NO: 2, (ii') a variable light domain region comprising the amino acid sequence of SEQ ID NO: 4, or (iii') a variable heavy domain region comprising the amino acid sequence of SEQ ID NO: 2 and a variable light domain region comprising the amino acid sequence of SEQ ID NO: 4, (ii) a pharmaceutically acceptable carrier, diluent, and/or excipient, and (iii) optionally, another active agent and/or an adjuvant, wherein the pharmaceutical composition is optionally part of a kit comprising one or more containers in which the antibody, another active agent and/or the adjuvant can be present in the same or different containers.

* * * * *